(12) United States Patent
Thompson

(10) Patent No.: US 12,644,124 B2
(45) Date of Patent: Jun. 2, 2026

(54) COMPOSITION FOR REGULATING PRODUCTION OF INTERFERING RIBONUCLEIC ACID

(71) Applicant: Wyvern Pharmaceuticals Inc., Calgary (CA)

(72) Inventor: Bradley G. Thompson, Calgary (CA)

(73) Assignee: Wyvern Pharmaceuticals Inc., Calgary (CA)

( * ) Notice: Subject to any disclaimer, the term of this patent is extended or adjusted under 35 U.S.C. 154(b) by 0 days.

(21) Appl. No.: 19/230,651

(22) Filed: Jun. 6, 2025

(65) Prior Publication Data

US 2025/0304971 A1    Oct. 2, 2025

Related U.S. Application Data

(60) Continuation of application No. 18/968,602, filed on Dec. 4, 2024, now Pat. No. 12,540,328, which is a division of application No. 18/582,272, filed on Feb. 20, 2024, now Pat. No. 12,522,831.

(51) Int. Cl.
*C12N 15/113* (2010.01)
*C12N 15/86* (2006.01)

(52) U.S. Cl.
CPC .......... *C12N 15/1138* (2013.01); *C12N 15/86* (2013.01); *C12N 2310/141* (2013.01); *C12N 2750/14143* (2013.01)

(58) Field of Classification Search
CPC .................. C12N 15/86; C12N 15/111; C12N 2310/141; C12N 2750/14141
See application file for complete search history.

(56) References Cited

U.S. PATENT DOCUMENTS

| | | | |
|---|---|---|---|
| 11,085,055 B2 | 8/2021 | Mallol et al. | |
| 11,162,102 B2 * | 11/2021 | Minshull .............. | C12N 9/1241 |
| 11,530,423 B1 | 12/2022 | Thompson | |
| 11,873,505 B2 | 1/2024 | Thompson | |
| 12,018,274 B2 | 6/2024 | Thompson | |
| 12,195,747 B1 | 1/2025 | Thompson | |
| 12,281,309 B1 | 4/2025 | Thompson | |
| 2016/0304869 A1 | 10/2016 | Maclean et al. | |
| 2024/0026377 A1 | 1/2024 | Thompson | |

FOREIGN PATENT DOCUMENTS

CA           2721333 A1    10/2009

OTHER PUBLICATIONS

Van den Berg, et al., pp. 1-12, Molecular Therapy—Nucleic Acids, vol. 5, 2016 (Year: 2016).*
Denzler R et al., Mol Cell. Nov. 3, 2016;64(3):565-579 (Year: 2016).*
Ying et al. 2008. Mol. Biotechnol. 38:257-268 (Year: 2008).*
Lam et al. 2015. Molec. Ther. Nuc. Ac. 4:e252 (Year: 2015).*
O'Brien et al. "Overview of microRNA biogenesis, mechanisms of actions, and circulation." Frontiers in endocrinology 9 (2018): 402.
Bofill-De Ros et al. "Guidelines for the optimal design of miRNA-based shRNAs." Methods 103 (2016): 157-166.
Denzler et al. "Impact of microRNA levels, target-site complementarity, and cooperativity on competing endogenous RNA-regulated gene expression." Molecular cell 64.3 (2016): 565-579.
Van Den Berg et al. "Design of effective primary microRNA mimics with different basal stem conformations." Molecular Therapy Nucleic Acids 5 (2016).
Nature (2010. Gene Expression. Scitable. Available online at Nature. com) <https://www.nature.com/scitable/topicpage/gene-expression-14121669> (2010).
Tritschler et al. "Concepts and limitations for learning developmental trajectories from single cell genomics." Development 146.12 (2019): dev170506.
Ying et al. "The microRNA (miRNA): overview of the RNA genes that modulate gene function." Molecular biotechnology 38 (2008): 257-268.
Lam et al. "siRNA versus miRNA as therapeutics for gene silencing." Molecular therapy Nucleic acids 4 (2015).
Zuo et al. "5—Hydroxytryptamine receptor 1D aggravates hepatocellular carcinoma progression through FoxO6 in AKT—dependent and independent manners." Hepatology 69.5 (2019): 2031-2047.
Volpicelli et al. "The micro RNA-29A modulates 5-HTR7 expression and its morphogenic effects in hippocampal neurons." (2019).
*Homo sapiens* 5HTR7, mRNA, NCBI Reference Sequence (2024).
Bottoni et al. "Targeting BTK through microRNA in chronic lymphocytic leukemia." Blood, The Journal of the American Society of Hematology 128.26 (2016): 3101-3112.
Brutons Tyrosine Kinase Genbank Sequence (2023).

(Continued)

*Primary Examiner* — Catherine Konopka
*Assistant Examiner* — Shabana S Meyering
(74) *Attorney, Agent, or Firm* — Gowling WLG (Canada) LLP

(57) ABSTRACT

Some embodiments of the present disclosure relate to one or more compositions that upregulate the production of one or more sequences of micro-interfering ribonucleic acid (miRNA). The sequences of miRNA may be complementary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a serotonin receptor, such as serotonin receptor 5HT1a, 5HT1b, 5HT1d, 5HT1e, 5HT1f, 5HT2a, 5HT2b, 5HT2c, 5HT3, 5HT4, 5HT6, or 5HT7.

2 Claims, No Drawings

Specification includes a Sequence Listing.

(56) References Cited

OTHER PUBLICATIONS

Christensen et al. "Recombinant adeno-associated virus-mediated microRNA delivery into the postnatal mouse brain reveals a role for miR-134 in dendritogenesis in vivo." Frontiers in neural circuits 3 (2010): 848.
*Homo sapiens* 5HT1a, mRNA, NCBI Reference Sequence NM_000524.4, 9 pages (Year: 2024).
Lundstrom K., Viruses. Mar. 7, 2023;15(3):698 (Year: 2023).
GenBank EGF Sequence (2023).
Ahmadzadeh et al. "BRAF mutation in hairy cell leukemia." Oncology reviews 8.2 (2014): 253.
Patton et al. "Biogenesis, delivery, and function of extracellular RNA." Journal of extracellular vesicles 4.1 (2015): 27494.
Clark et al. "Detection of BRAF splicing variants in plasma-derived cell-free nucleic acids and extracellular vesicles of melanoma patients failing targeted therapy therapies." Oncotarget 11.44 (2020): 4016.
NCBI search results for Seq ID No. 5 (2024).
NCBI Nucleotide Sequence ALK Lingand, search performed Dec. 26, 2024 (2023).
NCBI Nucleotide Sequence ALK Receptor, search performed Dec. 26, 2024 (2023).
GenBank EGFR Sequence (2023).
Genbank FLT3 Sequence (2024).
NCBI Nucleotide Sequence for PARP, search performed Dec. 26, 2024 (2024).
Kenji and Mizukami < star-protocols.cell.com/protocols/3185 >, Dec. 15, 2023, 17 pages, accessed on Sep. 9, 20225 (Year: 2023).
Kondratov et al. "Direct head-to-head evaluation of recombinant adeno-associated viral vectors manufactured in human versus insect cells." Molecular Therapy 25.12 (2017): 2661-2675.
Wang et al. "Adeno-associated virus vector as a platform for gene therapy delivery". Nat Rev Drug Discov. May 2019; 18(5):358-378. (Year: 2019).
Yang et al., Journal of Neuroimmunology, vol. 178, Issues 1-2, 2006, pp. 24-29, ISSN 0165-5728 (Year: 2006).
Millan, Current Opinion in Pharmacology, vol. 11, Issue 1, 2011, pp. 11-22, ISSN 1471-4892 (Year: 2011).
Francois (Journal of Neuroscience Sep. 19, 2018, 38 (38) 8200-8210) (Year: 2018).
Zuo X et al., Hepatology, 69 (5), 2031-2047 (Year: 2019).

\* cited by examiner

SEQUENCE LISTING

```
Sequence total quantity: 25
SEQ ID NO: 1            moltype = DNA   length = 5799
FEATURE                 Location/Qualifiers
source                  1..5799
                        mol_type = other DNA
                        organism = synthetic construct
SEQUENCE: 1
aatcaacctc tggattacaa aatttgtgaa agattgactg gtattcttaa ctatgttgct      60
ccttttacgc tatgtggata cgctgcttta atgcctttgt atcatgctat tgcttcccgt     120
atggctttca ttttctcctc cttgtataaa tcctggttgc tgtctctttta tgaggagttg     180
tggccgttg tcaggcaacg tggcgtggtg tgcactgtgt ttgctgacgc aaccccccact     240
ggttgggca ttgccaccac ctgtcagctc ctttccggga ctttcgcttt cccctccct      300
attgccacgg cggaactcat cgccgcctgc cttgcccgct gctggacagg ggctcggctg     360
ttgggcactg acaattccgt ggtgttgtcg gggaaatcat cgtcctttcc ttggctgctc     420
gcctgtgttg ccacctggat tctgcgcggg acgtccttct gctacgtccc ttcggccctc     480
aatccagcgg accttccttc ccgcggcctg ctgccggctc tgccggcctct tccgcgtctt     540
cgccttcgcc ctcagacgag tcggatctcc ctttgggccg cctccccgcc taagcttatc     600
gataccgtcg agatctaact tgtttattgc agcttataat ggttacaaat aaagcaatag     660
catcacaaat ttcacaaata aagcattttt ttcactgcat tctagttgtg gtttgtccaa     720
actcatcaat gtatcttatc atgtctggat ctcgacctcg actagagcat ggctacgtag     780
ataagtagca tggcgggtta atcattaact acaaggaacc cctagtgatg gagttggcca     840
ctccctctct gcgcgctcgc tcgctcactg aggccgggcg accaaaggtc gcccgacgcc     900
cgggctttgc ccgggcggcc tcagtgagcg agcgagcgcg cagctggcgt aatagcgaag     960
aggcccgcac cgatcgccct tcccaacagt tgcgcagcct gaatggcgaa tggcgattcc    1020
gttgcaatgg ctggcggtaa tattgttctg gatattacca gcaaggccga tagtttgagt    1080
tcttctactc aggcaagtga tgttattact aatcaaagaa gtattgcgac aacggttaat    1140
ttgcgtgatg gacagactct tttactcggt ggcctcactg attataaaaa cacttctcag    1200
gattctggcg taccgttcct gtctaaaatc cctttaatcg gcctcctgtt tagctcccgc    1260
tctgattcta acgaggaaag cacgttatac gtgctcgtca aagcaaccat agtacgcgcc    1320
ctgtagcggc gcattaagcg cggcgggtgt ggtggttacg cgcagcgtga ccgctacact    1380
tgccagcgcc ctagcgcccg ctcctttcgc tttcttccct tccttttctcg ccacgttcgc    1440
cggctttccc cgtcaagctc taaatcgggg ctcccctta gggttccgat ttagtgcttt    1500
acggcacctc gaccccaaaa aacttgatta gggtgatggt tcacgtagtg ggccatcgcc    1560
ctgatagacg gtttttcgcc ctttgacgtt ggagtccacg ttctttaata gtggactctt    1620
gttccaaact ggaacaacac tcaacccta t ctcggtctat tcttttgatt tataagggat    1680
tttgccgatt tcggcctatt ggttaaaaaa tgagctgatt taacaaaaat ttaacgcgaa    1740
ttttaacaaa atattaacgt ttacaattta aatatttgct tatacaatct tcctgttttt    1800
ggggcttttc tgattatcaa ccggggtaca tatgattgac atgctagttt tacgattacc    1860
gttcatcgat tctcttgttt gctccagact ctcaggcaat gacctgatag cctttgtaga    1920
```

-continued

```
gacctctcaa aaatagctac cctctccggc atgaatttat cagctagaac ggttgaatat    1980
catattgatg gtgatttgac tgtctccggc ctttctcacc cgtttgaatc tttacctaca    2040
cattactcag gcattgcatt taaaatatat gagggttcta aaaattttta tccttgcgtt    2100
gaaataaagg cttctcccgc aaaagtatta cagggtcata atgttttttgg tacaaccgat    2160
ttagctttat gctctgaggc tttattgctt aattttgcta attctttgcc ttgcctgtat    2220
gatttattgg atgttggaat tcctgatgcg gtattttctc cttacgcatc tgtgcggtat    2280
ttcacaccgc atatggtgca ctctcagtac aatctgctct gatgccgcat agttaagcca    2340
gccccgacac ccgccaacac ccgctgacgc gccctgacgg gcttgtctgc tcccggcatc    2400
cgcttacaga caagctgtga ccgtctccgg gagctgcatg tgtcagaggt tttcaccgtc    2460
atcaccgaaa cgcgcgagac gaaagggcct cgtgatacgc ctattttat aggttaatgt    2520
catgataata atggtttctt agacgtcagg tggcacttt cggggaaatg tgcgcggaac    2580
ccctatttgt ttatttttct aaatacattc aaatatgtat ccgctcatga gacaataacc    2640
ctgataaatg cttcaataat attgaaaaag gaagagtatg agtattcaac atttccgtgt    2700
cgcccttatt ccctttttg cggcattttg ccttcctgtt tttgctcacc cagaaacgct    2760
ggtgaaagta aaagatgctg aagatcagtt gggtgcacga gtgggttaca tcgaactgga    2820
tctcaacagc ggtaagatcc ttgagagttt tcgccccgaa gaacgttttc caatgatgag    2880
cacttttaaa gttctgctat gtggcgcggt attatcccgt attgacgccg ggcaagagca    2940
actcggtcgc cgcatacact attctcagaa tgacttggtt gagtactcac cagtcacaga    3000
aaagcatctt acggatggca tgacagtaag agaattatgc agtgctgcca taaccatgag    3060
tgataacact gcggccaact tacttctgac aacgatcgga ggaccgaagg agctaaccgc    3120
tttttttgcac aacatggggg atcatgtaac tcgccttgat cgttgggaac cggagctgaa    3180
tgaagccata ccaaacgacg agcgtgacac cacgatgcct gtagcaatgg caacaacgtt    3240
gcgcaaacta ttaactggcg aactacttac tctagcttcc cggcaacaat aatagactgg    3300
gatggaggcg gataaagttg caggaccact tctgcgctcg gcccttccgg ctggctggtt    3360
tattgctgat aaatctggag ccggtgagcg tgggtctcgc ggtatcattg cagcactggg    3420
gccagatggt aagccctccc gtatcgtagt tatctacacg acggggagtc aggcaactat    3480
ggatgaacga aatagacaga tcgctgagat aggtgcctca ctgattaagc attggtaact    3540
gtcagaccaa gtttactcat atatacttta gattgattta aaacttcatt tttaatttaa    3600
aaggatctag gtgaagatcc tttttgataa tctcatgacc aaaatccctt aacgtgagtt    3660
ttcgttccac tgagcgtcag accccgtaga aaagatcaaa ggatcttctt gagatccttt    3720
ttttctgcgc gtaatctgct gcttgcaaac aaaaaaacca ccgctaccag cggtggtttg    3780
tttgccggat caagagctac caactctttt tccgaaggta actggcttca gcagagcgca    3840
gataccaaat actgtccttc tagtgtagcc gtagttaggc caccacttca agaactctgt    3900
agcaccgcct acatacctcg ctctgctaat cctgttacca gtggctgctg ccagtggcga    3960
taagtcgtgt cttaccgggt tggactcaag acgatagtta ccggataagg cgcagcggtc    4020
gggctgaacg gggggttcgt gcacacagcc cagcttggag cgaacgacct acaccgaact    4080
gagataccta cagcgtgagc tatgagaaag cgccacgctt cccgaaggga aaaggcgga    4140
caggtatccg gtaagcggca gggtcggaac aggagagcgc acgagggagc ttccaggggg    4200
aaacgcctgg tatctttata gtcctgtcgg gtttcgccac ctctgacttg agcgtcgatt    4260
tttgtgatgc tcgtcagggg ggcggagcct atggaaaaac gccagcaacg cggcctttt    4320
acggttcctg gccttttgct ggccttttgc tcacatgttc tttcctgcgt tatcccctga    4380
ttctgtggat aaccgtatta ccgcctttga gtgagctgat accgctcgcc gcagccgaac    4440
gaccgagcgc agcgagtcag tgagcgagga agcggaagag cgcccaatac gcaaaccgcc    4500
tctccccgcg cgttggccga ttcattaatg cagcagctgc gcgctcgctc gctcactgag    4560
gccgcccggg caaagcccgg gcgtcgggcg acctttggtc gcccggcctc agtgagcgag    4620
cgagcgcgca gagagggagt ggccaactcc atcactaggg gttccttgta gttaatgatt    4680
aacccgccat gctacttatc tacgtagcca tgctctagga cattgattat tgactagtgg    4740
agttccgcgt tacataactt acggtaaatg gcccgcctgg ctgaccgccc aacgacccc    4800
gcccattgac gtcaataatg acgtatgttc ccatagtaac gccaataggg actttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gacctatggg actttcctta cttggcagta catctacgta ttagtcatcg    5040
ctattaccat ggtcgaggtg agccccacgt tctgcttcac tctccccatc tcccccccct    5100
ccccacccc aattttgtat ttatttatttt tttaattatt ttgtgcagcg atgggggcgg    5160
gggggggggg gggcgcgcgc caggcggggc ggggcggggc gagggggcgg gggcggcgag    5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aacccccagta tcagcagaag gacattttag gacgggactt gggtgactct agggcactgg    5640
ttttcttttcc agagagcgga acaggcgagg aaaagtagtc ccttctcggc gattctgcgg    5700
agggatctcc gtggggcggt gaacgccgat gatgcctcta ctaaccatgt tcatgtttc    5760
tttttttttc tacaggtcct gggtgacgaa cagggtacc    5799
```

SEQ ID NO: 2        moltype = DNA  length = 540
FEATURE            Location/Qualifiers
source             1..540
                    mol_type = other DNA
                    organism = synthetic construct
SEQUENCE: 2

```
gccaccatgg ccaccggctc tcgcacaagc ctgctgctgg cttttcggact gctgtgcctg     60
ccttggctcc aggagggctc cgccgctagc atcgataccg tcgctatgtg ctggaggctt    120
gctgaaggct gtatgctgat caatcggatt gcggtaatcg cgttttggcc tctgactgac    180
gcgattaccg atccgattga tcaggacaca aggcctgtta ctagcactca catgaacaa     240
atggcctcta gctggaggc ttgctgaagg ctgtatgctg atctttgcta aattggtgca    300
cgcgtttttg cctctgactg acgcgtgcac cattagcaaa gatcaggaca caaggcctgt    360
tactagcact cacatggaac aaatggcctc tagcctggag gcttgctgaa ggctgtatgc    420
```

-continued

```
tgacttcaat cacaattcca gcgccgtttt ggcctctgac tgacggcgct ggaagtgatt   480
gaagtcagga cacaaggcct gttactagca ctcacatgga acaaatggcc tctctagaat   540

SEQ ID NO: 3            moltype = DNA   length = 540
FEATURE                Location/Qualifiers
source                 1..540
                       mol_type = other DNA
                       organism = synthetic construct
SEQUENCE: 3
gccaccatgg ccaccggctc tcgcacaagc ctgctgctgg ctttcggact gctgtgcctg   60
ccttggctcc aggagggctc cgccgctagc atcgataccg tcgctatgtg ctggaggctt   120
gctgaaggct gtatgctgta atctttcgct ggctgcagtt cgtttttggc tctgactgac   180
gaactgcagc gcgaaagatt acaggacaca aggcctgtta ctagcactca catggaacaa   240
atggcctcta gcctggaggc ttgctgaagg ctgtatgctg tgttaatgct gatgtcacgc   300
tgcgttttgg cctctgactg acgcagcgtg accagcatta acacaggaca caaggcctg    360
tactagcact cacatggaac aaatggcctc tagcctggag gcttgctgaa ggctgtatgc   420
tgttcacctg gttaacacat acaccgtttt ggcctctgac tgacggtgta tgtgaaccag   480
gtgaacagga cacaaggcct gttactagca ctcacatgga acaaatggcc tctctagaat   540

SEQ ID NO: 4            moltype = DNA   length = 540
FEATURE                Location/Qualifiers
source                 1..540
                       mol_type = other DNA
                       organism = synthetic construct
SEQUENCE: 4
gccaccatgg ccaccggctc tcgcacaagc ctgctgctgg ctttcggact gctgtgcctg   60
ccttggctcc aggagggctc cgccgctagc atcgataccg tcgctatgtg ctggaggctt   120
gctgaaggct gtatgctgat ttcttcctgt gcgctttcgc cgtttttggc tctgactgac   180
ggcgaaagcg caggaagaaa tcaggacaca aggcctgtta ctagcactca catggaacaa   240
atggcctcta gcctggaggc ttgctgaagg ctgtatgctg agaataatca gatcagcacg   300
ctcgttttgg cctctgactg acgagcgtgc tgctgattat tctcaggaca caaggcctgt   360
tactagcact cacatggaac aaatggcctc tagcctggag gcttgctgaa ggctgtatgc   420
tgtaatcagg ctgaattcag atagcgtttt ggcctctgac tgacgctatc tgaacagcct   480
gattacagga cacaaggcct gttactagca ctcacatgga acaaatggcc tctctagaat   540

SEQ ID NO: 5            moltype = DNA   length = 540
FEATURE                Location/Qualifiers
source                 1..540
                       mol_type = other DNA
                       organism = synthetic construct
SEQUENCE: 5
gccaccatgg ccaccggctc tcgcacaagc ctgctgctgg ctttcggact gctgtgcctg   60
ccttggctcc aggagggctc cgccgctagc atcgataccg tcgctatgtg ctggaggctt   120
gctgaaggct gtatgctgat aatcaccgct gcaggttcag cgtttttggc tctgactgac   180
gctgaacctg gcggtgatta tcaggacaca aggcctgtta ctagcactca catggaacaa   240
atggcctcta gcctggaggc ttgctgaagg ctgtatgctg ttcaatcgcg tattggtaat   300
cgcgttttgg cctctgactg acgcgattac caacgcgatt gaacaggaca caaggcctgt   360
tactagcact cacatggaac aaatggcctc tagcctggag gcttgctgaa ggctgtatgc   420
tgtgatcatg ctgaaaatgg tgcacgtttt ggcctctgac tgacgtgcac cattcagcat   480
gatcacagga cacaaggcct gttactagca ctcacatgga acaaatggcc tctctagaat   540

SEQ ID NO: 6            moltype = DNA   length = 540
FEATURE                Location/Qualifiers
source                 1..540
                       mol_type = other DNA
                       organism = synthetic construct
SEQUENCE: 6
gccaccatgg ccaccggctc tcgcacaagc ctgctgctgg ctttcggact gctgtgcctg   60
ccttggctcc aggagggctc cgccgctagc atcgataccg tcgctatgtg ctggaggctt   120
gctgaaggct gtatgctgag gtaatatcct gacgctcagc cgtttttggc tctgactgac   180
ggctgagcgt ggatattacc tcaggacaca aggcctgtta ctagcactca catggaacaa   240
atggcctcta gcctggaggc ttgctgaagg ctgtatgctg tacagaatca gataatcagc   300
gccgttttgg cctctgactg acggcgctga ttctgattct gtacaggaca caaggcctgt   360
tactagcact cacatggaac aaatggcctc tagcctggag gcttgctgaa ggctgtatgc   420
tgtcatgttt aaaaattcgc tgcgcgtttt ggcctctgac tgacgcgcag cgaatttaaa   480
catgacagga cacaaggcct gttactagca ctcacatgga acaaatggcc tctctagaat   540

SEQ ID NO: 7            moltype = DNA   length = 540
FEATURE                Location/Qualifiers
source                 1..540
                       mol_type = other DNA
                       organism = synthetic construct
SEQUENCE: 7
gccaccatgg ccaccggctc tcgcacaagc ctgctgctgg ctttcggact gctgtgcctg   60
ccttggctcc aggagggctc cgccgctagc atcgataccg tcgctatgtg ctggaggctt   120
gctgaaggct gtatgctgat gaatcgggtt gtctgaatcg cgtttttggc tctgactgac   180
gcgattcaga acccgattca tcaggacaca aggcctgtta ctagcactca catggaacaa   240
atggcctcta gcctggaggc ttgctgaagg ctgtatgctg aacactttgc tatatcatcc   300
tgcgttttgg cctctgactg acgcaggatg atagcaaagt gttcaggaca caaggcctgt   360
```

```
tactagcact cacatggaac aaatggcctc tagcctggag gcttgctgaa ggctgtatgc  420
tgttctgttc gttaagctaa tgctcgtttt ggcctctgac tgacgagcat tagcaacgaa  480
cagaacagga cacaaggcct gttactagca ctcacatgga acaaatggcc tctctagaat  540

SEQ ID NO: 8              moltype = DNA   length = 540
FEATURE                   Location/Qualifiers
source                    1..540
                          mol_type = other DNA
                          organism = synthetic construct
SEQUENCE: 8
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgga gcattagcaa tgcgaacaga agtttttggcc tctgactgac  180
ttctgttcgt tgctaatgct ccaggacaca aggcctgtta ctagcactca catggaacaat  240
atggcctcta gcctggaggc ttgctgaagg ctgtatgctg aaacataatg gattcagcag  300
cgcgtttttgg cctctgactg acgcgctgct gaccattatg tttcaggaca caaggcctgt  360
tactagcact cacatggaac aaatggcctc tagcctggag gcttgctgaa ggctgtatgc  420
tgttatcttt gcgaagctgc catccgtttt ggcctctgac tgacgaatgg cagccgcaaa  480
gataacagga cacaaggcct gttactagca ctcacatgga acaaatggcc tctctagaat  540

SEQ ID NO: 9              moltype = DNA   length = 538
FEATURE                   Location/Qualifiers
source                    1..538
                          mol_type = other DNA
                          organism = synthetic construct
SEQUENCE: 9
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctggc tcctccactt ggtggtttgg ttttggcctc tgactgacgc  180
ggcaacattc tggtgattac aggacacaag gcctgttact agcactcaca tggaacaaat  240
ggcctctagc ctggaggctt gctgaaggct gtatgctgtc ataatcgcta tttggtgcgg  300
cgtttttggcc tctgactgac gccgcaccaa agcgattatg acaggacaca aggcctgtta  360
ctagcactca catggaacaa atggcctcta gcctggaggc ttgctgaagg ctgtatgctg  420
ttctgatcct gaagttcggg ttcgtttttgg cctctgactg acgaacccga accaggatca  480
gaacaggaca caaggcctgt tactagcact cacatggaac aaatggcctc tctagaat    538

SEQ ID NO: 10             moltype = DNA   length = 540
FEATURE                   Location/Qualifiers
source                    1..540
                          mol_type = other DNA
                          organism = synthetic construct
SEQUENCE: 10
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgaa atcttccggt ggttccactg cgtttttggcc tctgactgac  180
gcagtggaac ccgaagatt tcaggacaca aggcctgtta ctagcactca catggaacaa  240
atggcctcta gcctggaggc ttgctgaagg ctgtatgctg atatcctgaa tatggtatgc  300
agcgtttttgg cctctgactg acgctgcata ccattcagga tatcaggaca caaggcctgt  360
tactagcact cacatggaac aaatggcctc tagcctggag gcttgctgaa ggctgtatgc  420
tgtttaaagc tcaaacgcgt tcgccgtttt ggcctctgac tgacggcgaa cgcgtgagct  480
ttaaacagga cacaaggcct gttactagca ctcacatgga acaaatggcc tctctagaat  540

SEQ ID NO: 11             moltype = DNA   length = 540
FEATURE                   Location/Qualifiers
source                    1..540
                          mol_type = other DNA
                          organism = synthetic construct
SEQUENCE: 11
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgta ataaaggtct gggaatcacc cgtttttggcc tctgactgac  180
gggtgattcc gacctttatt acaggacaca aggcctgtta ctagcactca catggaacaa  240
atggcctcta gcctggaggc ttgctgaagg ctgtatgctg taatacgcca gatcaccatc  300
agcgtttttgg cctctgactg acgctgatgg tgctggcgta ttacaggaca caaggcctgt  360
tactagcact cacatggaac aaatggcctc tagcctggag gcttgctgaa ggctgtatgc  420
tgatacagaa acgaaggttc aggccgtttt ggcctctgac tgacggcctg aacccgtttc  480
tgtatcagga cacaaggcct gttactagca ctcacatgga acaaatggcc tctctagaat  540

SEQ ID NO: 12             moltype = DNA   length = 540
FEATURE                   Location/Qualifiers
source                    1..540
                          mol_type = other DNA
                          organism = synthetic construct
SEQUENCE: 12
gccaccatgg ccaccggctc tcgcacaagc ctgctgctgg ctttcggact gctgtgcctg  60
ccttggctcc aggagggctc cgccgctagc atcgataccg tcgctatgtg ctggaggctt  120
gctgaaggct gtatgctgtc agatcgctgt ggtaaacagg cgtttttggcc tctgactgac  180
gcctgtttac cagcgatctg acaggacaca aggcctgtta ctagcactca catggaacaa  240
atggcctcta gcctggaggc ttgctgaagg ctgtatgctg agaatcagat cagatagcga  300
```

```
tccgttttgg cctctgactg acggatcgct atctgctgat tctcaggaca caaggcctgt    360
tactagcact cacatggaac aaatggcctc tagcctggag gcttgctgaa ggctgtatgc    420
tgaaacatgc caacagcaga atgccgtttt ggcctctgac tgacggcatt ctgctgggca    480
tgtttcagga cacaaggcct gttactagca ctcacatgga acaaatggcc tctctagaat    540

SEQ ID NO: 13          moltype = DNA   length = 540
FEATURE                Location/Qualifiers
source                 1..540
                       mol_type = other DNA
                       organism = synthetic construct
SEQUENCE: 13
gccaccatgg ccaccggctc tcgcacaagc ctgctgctgg ctttcggact gctgtgcctg     60
ccttggctcc aggagggctc cgccgctagc atcgataccg tcgctatgtg ctggaggctt    120
gctgaaggct gtatgctgac aatcagatat ggttgctcgg cgtttggcc tctgactgac      180
gccgagcaac tatctgattg tcaggacaca aggcctgtta ctagcactca catgaacaa      240
atggcctcta gcctggaggc ttgctgaagg ctgtatgctg tttcacaatg catcgttcag    300
cgcgttttgg cctctgactg acgcgctgaa cggcattgtg aaacaggaca caaggcctgt    360
tactagcact cacatggaac aaatggcctc tagcctggag gcttgctgaa ggctgtatgc    420
tgacaataat gccaacaggg tggtcgtttt ggcctctgac tgacgaccac cctgggcatt    480
attgtcagga cacaaggcct gttactagca ctcacatgga acaaatggcc tctctagaat    540

SEQ ID NO: 14          moltype = DNA   length = 6339
FEATURE                Location/Qualifiers
source                 1..6339
                       mol_type = other DNA
                       organism = synthetic construct
SEQUENCE: 14
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctccctta gggttccgat ttagtgcttt    1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaatttttta tccttgcgtt   2100
gaaataaagg cttctcccgc aaaagtatta cagggtcata atgtttttgg tacaaccgat   2160
ttagctttat gctctgaggc tttattgctt aattttgcc attcttttgcc ttgcctgtat   2220
gatttattgg atgttggaat cctgatgcg tattttctc cttacgcatc tgtgcggtat     2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga caataacc     2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
```

-continued

```
tttttttgcac aacatggggg atcatgtaac tcgccttgat cgttgggaac cggagctgaa    3180
tgaagccata ccaaacgacg agcgtgacac cacgatgcct gtagcaatgg caacaacgtt    3240
gcgcaaacta ttaactggcg aactacttac tctagcttcc cggcaacaat taatagactg    3300
gatggaggcg gataaagttg caggaccact tctgcgctcg gcccttccgg ctggctggtt    3360
tattgctgat aaatctggag ccggtgagcg tgggtctcgc ggtatcattg cagcactggg    3420
gccagatggt aagccctccc gtatcgtagt tatctcacg acggggagtc aggcaactat    3480
ggatgaacga aatagacaga tcgctgagat aggtgcctca ctgattaagc attggtaact    3540
gtcagaccaa gtttactcat atatacttta gattgattta aaacttcatt tttaatttaa    3600
aaggatctag gtgaagatcc ttttttgataa tctcatgacc aaaatccctt aacgtgagtt    3660
ttcgttccac tgagcgtcag acccccgtaga aaagatcaaa ggatcttctt gagatccttt    3720
ttttctgcgc gtaatctgct gcttgcaaac aaaaaaacca ccgctaccag cggtggtttg    3780
tttgccggat caagagctac caactctttt tccgaaggta actggcttca gcagagcgca    3840
gataccaaat actgtccttc tagtgtagcc gtagttaggc caccacttca agaactctgt    3900
agcaccgcct acatacctcg ctctgctaat cctgttacca gtggctgctg ccagtggcga    3960
taagtcgtgt cttaccgggt tggactcaag acgatagtta ccggataagg cgcagcggtc    4020
gggctgaacg gggggttcgt gcacacagcc cagcttggag cgaacgacct acaccgaact    4080
gagatacctac agcgtgagc tatgagaaag cgccacgctt cccgaaggga gaaaggcgga    4140
caggtatccg gtaagcggca gggtcggaac aggagagcgc acgagggagc ttccaggggg    4200
aaacgcctgg tatctttata gtcctgtcgg gtttcgccac ctctgacttg agcgtcgatt    4260
tttgtgatgc tcgtcagggg ggcggagcct atggaaaaac gccagcaacg cggcctttt    4320
acggttcctg gccttttgct ggcctttt gc tcacatgttc tttcctgcgt tatccctga    4380
ttctgtggat aaccgtatta ccgcctttga gtgagctgat accgctcgcc gcagccgaac    4440
gaccgagcgc agcgagtcag tgagcgagga agcggaagac cgcccaatac gcaaaccgcc    4500
tctcccgcg cgttggccga ttcattaatg cagcagctgc gcgctcgctc gctcactgag    4560
gccgcccggg caaagcccgg gcgtcgggcg acctttggtc gcccggcctc agtgagcgag    4620
cgagcgcgca gagagggagt ggccaactcc atcactacgg gttccttgta gttaatgatt    4680
aacccgccat gctacttatc tacgtagcca tgctctagga cattgattat tgactagtag    4740
agttccgcgt tacataactt acggtaaatg gcccgcctgg ctgaccgccc aacgacccc    4800
gcccattgac gtcaataatg acgtatgttc ccatagtaac gccaataggg actttccatt    4860
gacgtcaatg ggtggagtat ttacggtaaa ctgcccactt ggcagtacat caagtgtatc    4920
atatgccaag tacgccccct attgacgtca atgacggtaa atggcccgcc tggcattatg    4980
cccagtacat gaccttatgg gactttccta cttggcagta catctacgta ttagtcatcg    5040
ctattaccat ggtcgaggtg agccccacgt tctgcttcac tctccccatc tccccccct    5100
cccaccccc aattttgtat ttatttattt ttgtgcagcg atggggggcgg    5160
ggggggggg gggcgcgcgc caggcggggc ggggcggggc gaggggcggg gcgggggcagg    5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgac ccgggtttg ggcctcccg    5460
cgggcgcccc cctcctcacg gcgagcgctg ccacgtcaga cgaagggcgc agcgagcgtc    5520
ctgatccttc cgcccggacg ctcaggacag cggcccgctg ctcataagac tcggccttag    5580
aaccccagta tcagcagaag gacattttag gacgggactt gggtgactct agggcactgg    5640
ttttcttcc agagagcgga acaggcgagg aaaagtagtc ccttctcggc gattctgcgg    5700
agggatctcc gtggggcggt gaacgccgat gatgcctcta ctaaccatgt tcatgttttc    5760
ttttttttc tacaggtcct gggtgacgaa cagggtaccg ccaccatggc caccggctct    5820
cgcacaagcc tgctgctggc tttcggactg ctgtgcctgc cttggctcca ggagggctcc    5880
gccgctagca tcgataccgt cgctatgtgc tggaggcttg ctgaaggctg tatgctgatc    5940
aatcggattg cggtaatcgc gttttggcct ctgactgacg cgattaccga tccgattgat    6000
caggacacaa ggcctgttac tagcactcac atggaacaaa tggcctctag cctgaggct    6060
tgctgaaggc tgtatgctga tctttgctaa attggtgcac gcgttttggc ctctgactga    6120
cgcgtgcacc attagcaaag atcaggacac aaggcctgtt actagcactc acatggaaca    6180
aatggcctct agcctggagg cttgctgaag gctgtatgct gacttcaatc acaattccag    6240
cgccgttttg gcctctgact gacgcgctg gaagtgattg aagtcaggac acaaggcctg    6300
ttactagcac tcacatggaa caaatggcct ctctagaat                           6339
```

SEQ ID NO: 15          moltype = DNA   length = 6339
FEATURE                Location/Qualifiers
source                 1..6339
                       mol_type = other DNA
                       organism = synthetic construct
SEQUENCE: 15

```
aatcaacctc tggattacaa aatttgtgaa agattgactg gtattcttaa ctatgttgct    60
cctttacgc tatgtggata cgctgcttta atgcctttgt atcatgctat tgcttcccgt    120
atggctttca ttttctcctc cttgtataaa tcctggttgc tgtctctta tgaggagttg    180
tggcccgttg tcaggcaacg tggcgtggtg tgcactgtgt ttgctgacgc aaccccact    240
ggttggggca ttgccaccac ctgtcagctc ctttccggga ctttcgcttt ccccctccct    300
attgccacgt cggaactcat cgccgcctgc cttcccgct gctggacagg ggctcggctg    360
ttgggcactg acaattccgt ggtgttgtcg gggaaatcat cgtccttttc cttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc gtatctggat ctcgacctcg actagagcat ggctacgtag    780
ataagtagca tggcgggtta atcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc    1020
gttgcaatgg ctggcggtaa tattgttctg gatattacca gcaaggccga tagtttgagt    1080
```

-continued

```
tcttctactc aggcaagtga tgttattact aatcaaagaa gtattgcgac aacggttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcggc gcattaagcg cggcgggtgt ggtggttacg gcagcgtga ccgctacact 1380
tgccagcgcc ctagcgcccg ctcctttcgc tttcttccct tcctttctcg ccacgttcgc 1440
cggctttccc cgtcaagctc taaatcgggg gctcccttta gggttccgat ttagtgcttt 1500
acggcacctc gaccccaaaa aacttgatta gggtgatggt tcacgtagtg ggccatcgcc 1560
ctgatagacg gtttttcgcc ctttgacgtt ggagtccacg ttctttaata gtggactctt 1620
gttccaaact ggaacaacac tcaaccctat ctcggtctat tcttttgatt tataagggat 1680
tttgccgatt tcggcctatt ggttaaaaaa tgagctgatt taacaaaaat ttaacgcgaa 1740
ttttaacaaa atattaacgt ttacaattta aatatttgct tatacaatct tcctgttttt 1800
ggggcttttc tgattatcaa ccggggtaca tatgattgac atgctagttt tacgattacc 1860
gttcatcgat tctcttgttt gctccagact ctcaggcaat gacctgatag ccttttgtaga 1920
gacctctcaa aaatagctac cctctccggc atgaatttat cagctagaac ggttgaaatat 1980
catattgatg gtgatttgac tgtctccggc ctttctcacc cgtttgaatc tttacctaca 2040
cattactcag gcattgcatt taaaatatat gagggttcta aaaattttta tccttgcgtt 2100
gaaataaagg cttctcccgc aaaagtatta cagggtcata atgttttttgg tacaaccgat 2160
ttagctttat gctctgaggc tttattgctt aattttgcta attctttgcc ttgcctgtat 2220
gatttattgg atgttggaat tcctgatgcg gtattttctc cttacgcatc tgtgcggtat 2280
ttcacaccgc atatggtgca ctctcagtac aatctgctct gatgccgcat agttaagcca 2340
gccccgacac ccgccaacac ccgctgacgc gccctgacgg gcttgtctgc tcccggcatc 2400
cgcttacaga caagctgtga ccgtctccgg gagctgcatg tgtcagaggt tttcaccgtc 2460
atcaccgaaa cgcgcgagac gaaagggcct cgtgatacgc ctatttttat aggttaatgt 2520
catgataata atggtttctt agacgtcagg tggcactttt cggggaaatg tgcgcggaac 2580
ccctatttgt ttatttttct aaatacattc aaatatgtat ccgctcatga gacaataacc 2640
ctgataaatg cttcaataat attgaaaaag gaagagtatg agtattcaac atttccgtgt 2700
cgcccttatt cccttttttg cggcattttg ccttcctgtt tttgctcacc cagaaacgct 2760
ggtgaaagta aaagatgctg aagatcagtt gggtgcacga gtgggttaca tcgaactgga 2820
tctcaacagc ggtaagatcc ttgagagttt tcgccccgaa gaacgttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060
tgataacact gcggccaact tacttctgac aacgatcgga ggaccgaagg agctaaccgc 3120
tttttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aaagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagataccta cagcgtgagc tatgagaaag cgccacgctt cccgaaggga gaaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg ggcggagcct atggaaaaac gccagcaacg cggcctttt 4320
acggttcctg gccttttgct ggccttttgc tcacatgttc tttcctgcgt tatccctgat 4380
ttctgtggat aaccgtatta ccgcctttga gtgagctgat accgctcgcc gcagccgaac 4440
gaccgagcgc agcgagtcag tgagcgagga agcggaagag cgcccaatac gcaaaccgcc 4500
tctccccgcg cgttggccga ttcattaatg cagcagctgc gcgctcgctc gctcactgag 4560
gccgcccggg caaagcccgg gcgtcgggcg acctttggtc gcccggcctc agtgagcgag 4620
cgagcgcgca gagagggagt ggccaactcc atcactaggg gttccttgta gttaatgatt 4680
aacccgccat gctacttatc tacgtagcca tgctctagga cattgattat tgactagtgg 4740
agttccgcgt tacataactt acggtaaatg gcccgcctgg ctgaccgccc aacgacccc 4800
gcccattgac gtcaataatg acgtatgttc ccatagtaac gccaataggg actttccatt 4860
gacgtcaatg ggtggagtat ttacggtaaa ctgcccactt ggcagtacat caagtgtatc 4920
atatgccaag tacgcccct attgacgtca atgacgtaa atggcccgcc tggcattatg 4980
cccagtacat gaccttatgg gactttccta cttggcagta catctacgta ttagtcatcg 5040
ctattaccat ggtcgaggtg agccccacgt tctgcttcac tctccccatc tccccccct 5100
cccccacccc aattttgtat ttatttattt ttaattattt ttgtgcagcg atggggggcgg 5160
gggggggggg gggcgcgcgc caggcggggc ggggcgggc gaggggcggg gcggggcgag 5220
gcggagaggg gcggcggcag ccaatcagag cggcgcgctc cgaaagtttc cttttatggc 5280
gaggcggcgg cggcggcggc cctataaaaa gcgaagcgcg cggcgggcgg gagtcgctgc 5340
gcgctgcctt cgccccgtgc cccgctccgc cgccgcctcg cgccgcccgc cccggctctg 5400
actgaccgcg ttactaaaac aggtaagtcc ggcctccgcg ccgggttttg gcgcctcccg 5460
cgggcgcccc cctcctcacg gcgagcgctg ccacgtcaga caaggcgcgc agcgagcgtc 5520
ctgatccttc cgcccggacg ctcaggacag cggcccgctg ctcataagac tcggccttag 5580
aacccccagta tcagcagaag gacattttag gacgggactt gggtgactct agggcactgg 5640
tttttctttcc agagagcgga acaggcgagg aaaagtagtc ccttctcggc gattctgcgg 5700
agggatctcc gtggggcggt gaacgccgat gatgcctcta ctaaccatgt tcatgttttc 5760
ttttttttttc tacaggtcct gggtgacgaa cagggtaccg ccaccatggc caccggctct 5820
```

-continued

```
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtaa   5940
tctttcgctg gctgcagttc gttttggcct ctgactgacg aactgcagcg cgaaagatta   6000
caggacacaa ggcctgttac tagcactcac atggaacaaa tggcctctag cctggaggct   6060
tgctgaaggc tgtatgctgt gttaatgctg atgtcacgct gcgtttttggc ctctgactga   6120
cgcagcgtga ccagcattaa cacaggacac aaggcctgtt actagcactc acatggaaca   6180
aatggcctct agcctggagg cttgctgaag gctgtatgct gttcacctgg ttaacacata   6240
caccgttttg gcctctgact gacggtgtat gtgaaccagg tgaacaggac acaaggcctg   6300
ttactagcac tcacatggaa caaatggcct ctctagaat                           6339
```

```
SEQ ID NO: 16            moltype = DNA   length = 6339
FEATURE                  Location/Qualifiers
source                   1..6339
                         mol_type = other DNA
                         organism = synthetic construct
SEQUENCE: 16
aatcaacctc tggattacaa aatttgtgaa agattgactg gtattcttaa ctatgttgct   60
cctttacgc tatgtggata cgctgcttta atgcctttgt atcatgctat tgcttcccgt    120
atggctttca ttttctcctc cttgtataaa tcctggttgc tgtctctttta tgaggagttg   180
tggcccgttg tcaggcaacg tggcgtggtg tgcactgtgt ttgctgacgc aaccccccact  240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctcccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattcgac aacggttaat    1140
ttgcgtgatg gacagactct tttactcggg ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctcccttta gggttccgat ttagtgcttt    1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattctcag gcattgcatt taaaatatat gagggttcta aaaattttta tcctttgacgt  2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat cctgatgcg gtattttctc cttacgcatc tgtgcggtat    2280
ttcacaccgc atatggtgca ctctcagtac aatctgctct gatgccgcat agttaagcca   2340
gccccgacac ccgccaacac ccgctgacg gccctgacgg gcttgtctgc tcccggcatc    2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt    2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttg cggcattttg ccttcctgtt tttgctcacc cagaaacgct    2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cactttaaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgag   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatgaggcg ataaagttg caggaccact tctgcgctcg gcccttccgg ctggctggtt     3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
```

```
tttgccggat  caagagctac  caactctttt  tccgaaggta  actggcttca  gcagagcgca  3840
gataccaaat  actgtccttc  tagtgtagcc  gtagttaggc  caccacttca  agaactctgt  3900
agcaccgcct  acatacctcg  ctctgctaat  cctgttacca  gtggctgctg  ccagtggcga  3960
taagtcgtgt  cttaccgggt  tggactcaag  acgatagtta  ccggataagg  cgcagcggtc  4020
gggctgaacg  gggggttcgt  gcacacagcc  cagcttggag  cgaacgacct  acaccgaact  4080
gagataccta  cagcgtgagc  tatgagaaag  cgccacgctt  cccgaaggga  gaaaggcgga  4140
caggtatccg  gtaagcggca  gggtcggaac  aggagagcgc  acgagggagc  ttccagggggg  4200
aaacgcctgg  tatctttata  gtcctgtcgg  gtttcgccac  ctctgacttg  agcgtcgatt  4260
tttgtgatgc  tcgtcagggg  ggcggagcct  atggaaaaac  gccagcaacg  cggccttttt  4320
acggttcctg  gccttttgct  ggcctttttgc  tcacatgttc  tttcctgcgt  tatcccctga  4380
ttctgtggat  aaccgtatta  ccgcctttga  gtgagctgat  accgctcgcc  gcagccgaac  4440
gaccgagcgc  agcgagtcag  tgagcgagga  agcggaagag  cgcccaatac  gcaaaccgcc  4500
tctccccgcg  cgttggccga  ttcattaatg  cagcagctgc  gcgctcgctc  gctcactgag  4560
gccgcccggg  caaagcccgg  gcgtcgggcg  acctttgtc  gcccggcctc  agtgagcgag  4620
cgagcgcgca  gagagggagt  ggccaactcc  atcactaggg  gttccttgta  gttaatgatt  4680
aacccgccat  gctacttatc  tacgtagcca  tgctctagga  cattgattat  tgactagtgg  4740
agttccgcgt  tacataactt  acggtaaatg  gcccgcctgg  ctgaccgccc  aacgacccc  4800
gcccattgac  gtcaataatg  acgtatgttc  ccatagtaac  gccaataggg  actttccatt  4860
gacgtcaatg  ggtggagtat  ttacggtaaa  ctgcccactt  ggcagtacat  caagtgtatc  4920
atatgccaag  tacgccccct  attgacgtca  atgacggtaa  atggcccgcc  tggcattatg  4980
cccagtacat  gaccttatgg  gactttccta  cttggcagta  catctacgta  ttagtcatcg  5040
ctattaccat  ggtcgaggtg  agccccacgt  tctgcttcac  tctcccccat  tccccccct  5100
ccccacccc  aattttgtat  ttatttattt  tttaattatt  ttgtgcagcg  atggggggcgg  5160
ggggggggggg  gggcgcgcgc  caggcggggc  ggggcggggc  gaggggcggg  gcggggcgag  5220
gcggagaggt  gcggcggcag  ccaatcagag  cggcgcgctc  cgaaagtttc  cttttatggc  5280
gaggcggcgg  cggcggcggc  cctataaaaa  gcgaagcgcg  cggcgggcgg  gagtcgctgc  5340
gcgctgcctt  cgccccgtgc  ccgctccgc  cgccgcctcg  cgccgcccgc  cccggctctg  5400
actgaccgcg  ttactaaaac  aggtaagtcc  ggcctccgcg  ccgggttttg  gcgcctcccg  5460
cgggcgcccc  cctcctcacg  gcgagcgctg  ccacgtcaga  cgaagggcgc  agcgagcgtc  5520
ctgatccttc  cgcccggacg  ctcaggacag  cggcccgctc  ctcataagac  tcggccttag  5580
aaccccagta  tcagcagaag  gacattttag  gacgggactt  gggtgactct  agggcactgg  5640
ttttctttcc  agagagcgga  acaggcgagg  aaaagtagtc  ccttctcggc  gattctgcgg  5700
agggatctcc  gtggggcggt  gaacgccgat  gatgcctcta  ctaaccatgt  tcatgttttc  5760
tttttttttc  tacaggtcct  gggtgacgaa  cagggtaccg  ccaccatgc  caccggctct  5820
cgcacaagcc  tgctgctggc  tttcggactg  ctgtgcctgc  cttggctcca  ggagggctcc  5880
gccgctagca  tcgataccgt  cgctatgtgc  tggaggcttg  ctgaaggctg  tatgctgatt  5940
tcttcctgtg  cgctttcgcc  gttttggcct  ctgactgacg  gcgaaagcgc  aggaagaaat  6000
caggacacaa  ggcctgttac  tagcactcac  atggaacaaa  tggcctctag  cctggaggct  6060
tgctgaacaa  tgtatgctga  gaataatcag  atcagcacgc  tcgtttttgc  ctctgactag  6120
cgagcgtgct  gctgattatt  ctcaggcacc  aaggcctgtt  actagcactc  acatggaaca  6180
aatgccctct  agcctggagg  cttgctgaag  gctgtatgct  gtaatcaggc  tgaattcaga  6240
tagcgttttg  gcctctgact  gacgctatct  gaacagcctg  attacaggac  acaaggcctg  6300
ttactagcac  tcacatggaa  caaatggcct  ctctagaat              6339
```

SEQ ID NO: 17        moltype = DNA   length = 6339
FEATURE              Location/Qualifiers
source               1..6339
                     mol_type = other DNA
                     organism = synthetic construct

SEQUENCE: 17

```
aatcaacctc  tggattacaa  aatttgtgaa  agattgactg  gtattcttaa  ctatgttgct  60
ccttttacgc  tatgtggata  cgctgcttta  atgcctttgt  atcatgctat  tgcttcccgt  120
atggctttca  ttttctcctc  cttgtataaa  tcctggttgc  tgtctcttta  tgaggagttg  180
tggcccgttg  tcaggcaacg  tggcgtggtg  tgcactgtgt  ttgctgacgc  aaccccccact  240
ggttggggca  ttgccaccac  ctgtcagctc  ctttccgctt  ctttcgcttt  ccccctcctt  300
attgccacgg  cggaactcat  cgccgcctgc  cttgcccgct  gctggacagg  ggctcggctg  360
ttgggcactg  acaattccgt  ggtgttgtcg  gggaaatcat  cgtcctttcc  ttggctgctc  420
gcctgtgttg  ccacctggat  tctgcgcggg  acgtccttct  gctacgtccc  ttcggccctc  480
aatccagcgg  accttccttc  ccgcggcctg  ctgccggctc  tgcggcctct  tccgcgtctt  540
cgccttcgcc  ctcagacgag  tcggatctcc  ctttgggccg  cctccccgcc  taagcttatc  600
gataccgtcg  agatctaact  tgtttattgc  agcttataat  ggttacaaat  aaagcaatag  660
catcacaaat  ttcacaaata  aagcattttt  ttcactgcat  tctagttgtg  gtttgtccaa  720
actcatcaat  gtatcttatc  atgtctggat  ctcgacctcg  actagagcat  ggctacgtag  780
ataagtagca  tggcgggtta  atcattaact  acaaggaacc  cctagtgatg  gagttggtcca  840
ctccctctct  gcgcgctcgc  tcgctcactg  aggccgggcg  accaaaggtc  gcccgacgcc  900
cgggctttgc  ccgggcggcc  tcagtgagcg  agcgagcgcg  cagctggcgt  aatagcgaag  960
aggcccgcac  cgatcgccct  tcccaacagt  tgcgcagcct  gaatggcgaa  tggcgattcc  1020
gttgcaatgg  ctggcggtaa  tattgttctg  gatattacca  gcaaggccga  tagtttgagt  1080
tcttctactc  aggcaagtga  tgttattact  aatcaaagaa  gtattgcgac  aacggttaat  1140
ttgcgtgatg  gacagactct  tttactcggt  ggcctcactg  attataaaaa  cacttctcag  1200
gattctggcg  taccgttcct  gtctaaaatc  cctttaatcg  gcctcctgtt  tagctcccgc  1260
tctgattcta  acgaggaaag  cacgttatac  gtgctcgtca  aagcaaccat  agtacgcgcc  1320
ctgtagcggc  gcattaagcg  cggcgggtgt  ggtggttacg  cgcagcgtga  ccgctacact  1380
tgccagcgcc  ctagcgcccg  ctcctttcgc  tttcttccct  tcctttctcg  ccacgttcgc  1440
cggctttccc  cgtcaagctc  taaatcgggg  gctcccttta  gggttccgat  ttagtgcttt  1500
acggcacctc  gaccccaaaa  aacttgatta  gggtgatggt  tcacgtagtg  ggccatcgcc  1560
ctgatagacg  gtttttcgcc  ctttgacgtt  ggagtccacg  ttctttaata  gtggactctt  1620
gttccaaact  ggaacaacac  tcaacccatt  ctcggtctat  tcttttgatt  tataagggat  1680
tttgccgatt  tcggcctatt  ggttaaaaaa  tgagctgatt  taacaaaaat  ttaacgcgaa  1740
```

-continued

```
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgttttggg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt    2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttg cggcattttg ccttcctgtt tttgctcacc cagaaacgct    2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacctta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt    4320
acggttcctg gccttttgct ggccttttgc tcacatgttc tttcctgcgt tatccccctga  4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcggcgc acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg    4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccaccccc aatttttgtat ttatttattt tttaattatt ttgtgcagcg atggggggcgg  5160
ggggggggggg gggcgcgcgc caggcgggggc ggggcggggc gaggggcggg gcggggcgag  5220
gcggagaggt gcggcggcag ccaatcagag cggcgcgctc cgaaagtttc cttttatggc    5280
gaggcggcgg cggcggcggc cctataaaaa gcgaagcgcg cggcgggcgg gagtcgctgc    5340
gcgctgcctt cgccccgtgc cccgctccgc cgccgcctcg cgccgcccgc cccggctctg    5400
actgaccgcg ttactaaaac aggtaagtcc ggcctccgcg ccgggttttg gcgcctcccg    5460
cgggcgcccc cctcctcacg gcgagcgctg ccacgtcaga cgaagggcgc agcgagcgtc    5520
ctgatccttc cgcccgaacg ctcaggacag cggcccgctg ctcataagac tcggccttag   5580
aaccccagta tcagcagaag gacattttag gacgggactt gggtgactct agggcactgg    5640
ttttctttcc agagagcgga acaggcgagg aaaagtagtc ccttctcggc gattctgcgg    5700
agggatctcc gtggggcggt gaacgccgat gatgcctcta ctaaccatgt tcatgttttc    5760
ttttttttc tacaggtcct gggtgacgaa cagggtaccg ccaccatggc caccggctct     5820
cgcacaagcc tgctgctggc tttcggactg ctgtgcctga cttggctcca ggagggctcc    5880
gccgctagca tcgataccgt cgctatgtgc tggaggcttg ctgaaggctg tatgctgata    5940
atcaccgctg caggttcagc gttttggcct ctgactgacg ctgaacctgg cggtgattat    6000
caggacacaa ggcctgttac tagcactcac atggaacaaa tggcctctag cctggaggct    6060
tgctgaaggc tgtatgctgt tcaatcgcgt attggtaatc gcgtttttggc ctctgactga   6120
cgcgattacc aacgcgattg aacaggacac aaggcctgtt actagcactc acatggaaca   6180
aatggcctct agcctggagg cttgctgaag gctgtatgct gtgatcatgc tgaaaatggt   6240
gcacgttttg gcctctgact gacgtgcacc attcagcatg atcacaggac acaaggcctg   6300
ttactagcac tcacatggaa caaatggcct ctctagaat                          6339
```

SEQ ID NO: 18        moltype = DNA  length = 6339

-continued

```
FEATURE          Location/Qualifiers
source           1..6339
                 mol_type = other DNA
                 organism = synthetic construct SEQUENCE: 18
aatcaacctc tggattacaa aatttgtgaa agattgactg gtattcttaa ctatgttgct   60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc taagcttatc  600
gataccgtcg agatctaact tgtttattgc agcttataat ggttacaaat aaagcaatag  660
catcacaaat ttcacaaata aagcattttt ttcactgcat tctagttgtg gtttgtccaa  720
actcatcaat gtatcttatc atgtctggat ctcgacctcg actagagcat ggctacgtag  780
ataagtagca tggcgggtta atcattaact acaaggaacc cctagtgatg gagttggcca  840
ctccctctct gcgcgctcgc tcgctcactg aggccgggcg accaaaggtc gcccgacgcc  900
cgggctttgc ccgggcggcc tcagtgagcg agcgagcgcg cagctggcgt aatagcgaag  960
aggcccgcac cgatcgccct tcccaacagt tgcgcagcct gaatggcgaa tggcgattcc 1020
gttgcaatgg ctggcggtaa tattgttctg gatattacca gcaaggccga tagtttgagt 1080
tcttctactc aggcaagtga tgttattact aatcaaagaa gtattgcgac aacggttaat 1140
ttgcgtgatg gacagactct tttactcggt ggcctcactg attataaaaa cacttctcag 1200
gattctggcg taccgttcct gtctaaaatc cctttaatcg gcctcctgtt tagctcccgc 1260
tctgattcta acgaggaaag cacgttatac gtgctcgtca aagcaaccat agtacgcgcc 1320
ctgtagcggc gcattaagcg cggcgggtgt ggtggttacg cgcagcgtga ccgctacact 1380
tgccagcgcc ctagcgcccg ctcctttcgc tttcttccct tcctttctcg ccacgttcgc 1440
cggctttccc cgtcaagctc taaatcgggg gctcccttta gggttccgat ttagtgcttt 1500
acggcacctc gaccccaaaa aacttgatta gggtgatggt tcacgtagtg ggccatcgcc 1560
ctgatagacg gtttttcgcc ctttgacgtt ggagtccacg ttctttaata gtggactctt 1620
gttccaaact ggaacaacac tcaaccctat ctcggtctat tcttttgatt tataagggat 1680
tttgccgatt tcggcctatt ggttaaaaaa tgagctgatt taacaaaaat ttaacgcgaa 1740
ttttaacaaa atattaacgt ttacaattta aatatttgct tatacaatct tcctgttttt 1800
ggggcttttc tgattatcaa ccggggtaca tatgattgac atgctagttt tacgattacc 1860
gttcatcgat tctcttgttt gctccagact ctcaggcaat gacctgatag cctttgtaga 1920
gacctctcaa aaatagctac cctctccggc atgaatttat cagctagaac ggttgaatat 1980
catattgatg gtgatttgac tgtctccggc ctttctcacc cgtttgaatc tttacctaca 2040
cattactcag gcattgcatt taaaatatat gagggttcta aaaattttta tccttgcgtt 2100
gaaataaagg cttctcccgc aaaagtatta cagggtcata atgtttttgg tacaaccgat 2160
ttagctttat gctctgaggc tttattgctt aattttgcta attctttgcc ttgcctgtat 2220
gatttattgg atgttggaat tcctgatgcg gtattttctc cttacgcatc tgtgcggtat 2280
ttcacaccgc atatggtgca ctctcagtac aatctgctct gatgccgcat agttaagcca 2340
gccccgacac ccgccaacac ccgctgacgc gccctgacgg gcttgtctgc tcccggcatc 2400
cgcttacaga caagctgtga ccgtctccgg gagctgcatg tgtcagaggt tttcaccgtc 2460
atcaccgaaa cgcgcgagac gaaagggcct cgtgatacgc ctattttat aggttaatgt 2520
catgataata atggtttctt agacgtcagg tggcactttt cggggaaatg tgcgcggaac 2580
ccctatttgt ttatttttct aaatacattc aaatatgtat ccgctcatga caataaacc  2640
ctgataaatg cttcaataat attgaaaaag gaagagtatg agtattcaac atttccgtgt 2700
cgcccttatt cccttttttg cggcattttg ccttcctgtt tttgctcacc cagaaacgct 2760
ggtgaaagta aaagatgctg aagatcagtt gggtgcacga gtgggttaca tcgaactgga 2820
tctcaacagc ggtaagatcc ttgagagttt tcgccccgaa gaacgttttc caatgatgag 2880
cacttttaaa gttctgctat gtggcgcggt attatcccgt attgacgccg ggcaagagca 2940
actcggtcgc cgcatacact attctcagaa tgacttggtt gagtactcac cagtcacaga 3000
aaagcatctt acggatggca tgacagtaag agaattatgc agtgctgcca taaccatgag 3060
tgataacact gcggccaact tacttctgac aacgatcgga ggaccgaagg agctaaccgc 3120
ttttttgcac aacatggggg atcatgtaac tcgccttgat cgttgggaac cggagctgaa 3180
tgaagccata ccaaacgacg agcgtgacac cacgatgcct gtagcaatgg caacaacgtt 3240
gcgcaaacta ttaactggcg aactacttac tctagcttcc cggcaacaat taatagactg 3300
gatggaggcg gataaagttg caggaccact tctgcgctcg gcccttccgg ctggctggtt 3360
tattgctgat aaatctggag ccggtgagcg tgggtctcgc ggtatcattg cagcactggg 3420
gccagatggt aagccctccc gtatcgtagt tatctacacg acggggagtc aggcaactat 3480
ggatgaacga aatagacaga tcgctgagat aggtgcctca ctgattaagc attggtaact 3540
gtcagaccaa gtttactcat atatacttta gattgattta aaacttcatt tttaatttaa 3600
aaggatctag gtgaagatcc tttttgataa tctcatgacc aaaatccctt aacgtgagtt 3660
ttcgttccac tgagcgtcag accccgtaga aaagatcaaa ggatcttctt gagatccttt 3720
ttttctgcgc gtaatctgct gcttgcaaac aaaaaaacca ccgctaccag cggtggtttg 3780
tttgccggat caagagctac caactctttt tccgaaggta actggcttca gcagagcgca 3840
gataccaaat actgtccttc tagtgtagcc gtagttaggc caccacttca agaactctgt 3900
agcaccgcct acatacctcg ctctgctaat cctgttacca gtggctgctg ccagtggcga 3960
taagtcgtgt cttaccgggt tggactcaag acgatagtta ccggataagg cgcagcggtc 4020
gggctgaacg gggggttcgt gcacacagcc cagcttggag cgaacgacct acaccgaact 4080
gagatacctg cagcgtgagc tatgagaaag cgccacgctt cccgaaggga gaaaggcgga 4140
caggtatccg gtaagcggca gggtcggaac aggagagcgc acgagggagc ttccaggggg 4200
aaacgcctgg tatctttata gtcctgtcgg gtttcgccac ctctgacttg agcgtcgatt 4260
tttgtgatgc tcgtcagggg ggcggagcct atggaaaaac gccagcaacg cggcctttt  4320
acggttcctg gccttttgct ggccttttgc tcacatgttc tttcctgcgt tatcccctga 4380
ttctgtggat aaccgtatta ccgcctttga gtgagctgat accgctcgcc gcagccgaac 4440
```

-continued

```
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc    4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg    4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atggggggcgg    5160
gggggggggg gggcgcgcgc caggcggggc ggggcggggc gaggggcggg gcggggcgag   5220
gcggagaggt gcggcggcag ccaatcagag cggcggcctc cgaaagtttc cttttatggc   5280
gaggcggcgg cggcggcggc cctataaaaa gcgaagcgcg cggcgggcgg gagtcgctgc   5340
gcgctgcctt cgcccgtgc cccgctccgc cgccgcctcg cgccgcccgc cccggctctg    5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgtttc    5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgagg   5940
taatatcctg acgctcagcc gttttggcct ctgactgacg gctgagccgg gatattacct   6000
caggacacaa ggcctgttac tagcactcac atggaacaaa tggcctctag cctggaggct   6060
tgctgaaggc tgtatgctgt acagaatcag ataatcagcg ccgttttggc ctctgactga   6120
cggcgctgat tctgattctg tacaggacac aaggcctgtt actagcactc acatggaaca   6180
aatggcctct agcctggagg cttgctgaag gctgtatgct gtcatgttta aaaattcgct   6240
gcgcgttttg gcctctgact gacgcgcagc gaatttaaac atgacaggac acaaggcctg   6300
ttactagcac tcacatggaa caaatggcct ctctagaat                          6339
```

```
SEQ ID NO: 19          moltype = DNA  length = 6339
FEATURE                Location/Qualifiers
source                 1..6339
                       mol_type = other DNA
                       organism = synthetic construct
SEQUENCE: 19
aatcaacctc tggattacaa aatttgtgaa agattgactg gtattcttaa ctatgttgct   60
cctttacgc tatgtggata cgctgcttta atgcctttgt atcatgctat tgcttccgt    120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcatttt ttcactgcat tctagttgtg gtttgtccaa    720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg atattacca gcaaggccga tagtttgagt    1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctccctta gttagtgctt               1500
acggcacctc gaccccaaaa aacttgatta gggtgatggt tcacgtagtg ggccatcgcc   1560
ctgatagacg gttttcgcc ctttgacgtt ggagtccacg ttctttaata gtggactctt    1620
gttccaaact ggaacaacac tcaaccctat ctcggtctat tcttttgatt tataaggat    1680
tttgccgatt tcggcctatt ggttaaaaaa tgagctgatt taacaaaaat ttaacgcgaa   1740
ttttaacaaa atattaacgt ttacaattta aatatttgct tatacaatct tcctgtttt    1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaattat cagctagaac ggttgaatat    1980
catattgatg gtgatttgac tgtctccggc ctttctcacc cgtttgaatc tttacctaca   2040
cattactcag gcattgcatt taaaatatat gagggttcata aaaatttta tccttgcgtt    2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
```

-continued

```
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttattttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccagggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgaccccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccce aattttgtat ttatttattt tttaattatt ttgtgcagcg atggggggcgg   5160
gggggggggg gggcgcgcgc caggcggggc ggggcgggag gagggcgggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagc tgctgctggc tttcggactg ctgtgcctgc cttggctcca ggagggctcc   5880
gccgctagca tcgataccgt cgctatgtgc tggaggcttg ctgaaggctg tatgctgatg   5940
aatcgggttg tctgaatcgc gttttggcct ctgactgacg cgattcagaa cccgattcat   6000
caggacacaa ggcctgttac tagcactcac atggaacaaa tggcctctag cctgaggct   6060
tgctgaaggc tgtatgctga acactttgct atatcatcct gcgttttggc ctctgactga   6120
cgcaggatga tagcaaagtg ttcaggacac aaggcctgtt actagcactc acatggaaca   6180
aatggcctct agcctggagg cttgctgaag gctgtatgct gttctgttcg ttaagctaat   6240
gctcgttttg gcctctgact gacgagcatt agcaacgaac agaacaggac acaaggcctg   6300
ttactagcac tcacatggaa caaatggcct ctctagaat                          6339
```

SEQ ID NO: 20           moltype = DNA  length = 6339
FEATURE                 Location/Qualifiers
source                  1..6339
                        mol_type = other DNA
                        organism = synthetic construct
SEQUENCE: 20

```
aatcaacctc tggattacaa aatttgtgaa agattgactg gtattcttaa ctatgttgct   60
cctttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
```

-continued

```
ttgggcactg acaattccgt ggtgttgtcg gggaaatcat cgtcctttcc ttggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc taagcttatc      600
gataccgtcg agatctaact tgtttattgc agcttataat ggttacaaat aaagcaatag      660
catcacaaat ttcacaaata aagcattttt ttcactgcat tctagttgtg gtttgtccaa      720
actcatcaat gtatcttatc atgtctggat ctcgacctcg actagagcat ggctacgtag      780
ataagtagca tggcgggtta atcattaact acaaggaacc cctagtgatg gagttggcca      840
ctccctctct gcgcgctcgc tcgctcactg aggccgggcg accaaaggtc gcccgacgcc      900
cgggctttgc ccgggcggcc tcagtgagcg agcgagcgcg cagctggcgt aatagcgaag      960
aggcccgcac cgatcgccct tcccaacagt tgcgcagcct gaatggcgaa tggcgattcc     1020
gttgcaatgc tggcggtaa tattgttctg gatattacca gcaaggccga tagtttgagt      1080
tcttctactc aggcaagtga tgttattact aatcaaagaa gtattgcgac aacggttaat     1140
ttgcgtgatg gacagactct tttactcggt ggcctcactg attataaaaa cacttctcag     1200
gattctggcg taccgttcct gtctaaaatc cctttaatcg gcctcctgtt tagctcccgc     1260
tctgattcta acgaggaaag cacgttatac gtgctcgtca aagcaaccat agtacgcgcc     1320
ctgtagcggc gcattaagcg cggcgggtgt ggtggttacg cgcagcgtga ccgctacact     1380
tgccagcgcc ctagcgcccg ctcctttcgc tttcttccct tcctttctcg ccacgttcgc     1440
cggctttccc cgtcaagctc taaatcgggg ctccctttta gggttccgat ttagtgcttt     1500
acggcacctc gaccccaaaa aacttgatta gggtgatggt tcacgtagtg ggccatcgcc     1560
ctgatagacg gttttttcgc ctttgacgtt ggagtccacg ttctttaata gtggactctt     1620
gttccaaact ggaacaacac tcaaccctat ctcggtctat tcttttgatt tataagggat     1680
tttgccgatt tcggcctatt ggttaaaaaa tgagctgatt taacaaaaat ttaacgcgaa     1740
ttttaacaaa atattaacgt ttacaattta aatatttgct tatacaatct tcctgttttt     1800
ggggcttttc tgattatcaa ccggggtaca tatgattgac atgctagttt tacgattacc     1860
gttcatcgat tctcttgttt gctccagact ctcaggcaat gacctgatag cctttgtaga     1920
gacctctcaa aaatagctac cctctccggc atgaatttat cagctagaac ggttgaatat     1980
catattgatg gtgatttgac tgtctccggc ctttctcacc cgtttgaatc tttacctaca     2040
cattactcag gcattgcatt taaaatatat gagggttcta aaaattttta tccttgcgtt     2100
gaaataaagg cttctcccgc aaaagtatta cagggtcata atgtttttgg tacaaccgat     2160
ttagctttat gctctgaggc tttattgctt aattttgcta attctttgcc ttgcctgtat     2220
gatttattgg atgttggaat tcctgatgcg gtatttttctc cttacgcatc tgtgcggtat     2280
ttcacaccgc atatggtgca ctctcagtac aatctgctct gatgccgcat agttaagcca     2340
gccccgacac ccgccaacac ccgctgacgc gccctgacgg gcttgtctgc tcccggcatc     2400
cgcttacaga caagctgtga ccgtctccgg gagctgcatg tgtcagaggt tttcaccgtc     2460
atcaccgaaa cgcgcgagac gaaagggcct cgtgatacgc ctatttttat aggttaatgt     2520
catgataata atggtttctt agacgtcagg tggcacttttt cggggaaatg tgcgcggaac     2580
ccctatttgt ttatttttct aaatacattc aaatatgtat ccgctcatga gacaataacc     2640
ctgataaatg cttcaataat attgaaaaag gaagagtatg agtattcaac atttccgtgt     2700
cgcccttatt cccttttttg cggcattttg ccttcctgtt tttgctcacc cagaaacgct     2760
ggtgaaagta aaagatgctg aagatcagtt gggtgcacga gtgggttaca tcgaactgga     2820
tctcaacagc ggtaagatcc ttgagagttt tcgccccgaa gaacgttttc caatgatgag     2880
cacttttaaa gttctgctat gtggcgcggt attatcccgt attgacgccg ggcaagagca     2940
actcggtcgc cgcatacact attctcagaa tgacttggtt gagtactcac cagtcacaga     3000
aaagcatctt acggatggca tgacagtaag agaattatgc agtgctgcca taaccatgag     3060
tgataacact gcggccaact tacttctgac aacgatcgga ggaccgaagg agctaaccgc     3120
tttttttgcac aacatggggg atcatgtaac tcgccttgat cgttgggaac cggagctgaa     3180
tgaagccata ccaaacgacg agcgtgacac cacgatgcct gtagcaatgg caacaacgtt     3240
gcgcaaacta ttaactggcg aactacttac tctagcttcc cggcaacaat taatagactg     3300
gatggaggcg gataaagttg caggaccact tctgcgctcg gcccttccgg ctggctggtt     3360
tattgctgat aaatctggag ccggtgagcg tgggtctcgc ggtatcattg cagcactggg     3420
gccagatggt aagccctccc gtatcgtagt tatctacacg acggggagtc aggcaactat     3480
ggatgaacga aatagacaga tcgctgagat aggtgcctca ctgattaagc attggtaact     3540
gtcagaccaa gtttactcat atatacttta gattgattta aaacttcatt tttaatttaa     3600
aaggatctag gtgaagatcc tttttgataa tctcatgacc aaaatccctt aacgtgagtt     3660
ttcgttccac tgagcgtcag accccgtaga aaagatcaaa ggatcttctt gagatccttt     3720
ttttctgcgc gtaatctgct gcttgcaaac aaaaaaacca ccgctaccag cggtggtttg     3780
tttgccggat caagagctac caactctttt tccgaaggta actggcttca gcagagcgca     3840
gataccaaat actgtccttc tagtgtagcc gtagttaggc caccacttca agaactctgt     3900
agcaccgcct acatacctcg ctctgctaat cctgttacca gtggctgctg ccagtggcga     3960
taagtcgtgt cttaccgggt tggactcaag acgatagtta ccggataagg cgcagcggtc     4020
gggctgaacg gggggttcgt gcacacagcc cagcttggag cgaacgacct acaccgaact     4080
gagatacctac cagcgtgagc tatgagaaag cgccacgctt cccgaaggga aaaggcgga     4140
caggtatccg gtaagcggca gggtcggaac aggagagcgc acgagggagc ttccagggga     4200
aaacgcctgg tatctttata gtcctgtcgg gtttcgccac ctctgacttg agcgtcgatt     4260
tttgtgatgc tcgtcagggg ggcggagcct atggaaaaac gccagcaacg cggccttttt     4320
acggttcctg gccttttgct ggccttttgc tcacatgttc tttcctgcgt tatccctga      4380
ttctgtggat aaccgtatta ccgcctttga gtgagctgat accgctcgcc gcagccgaac      4440
gaccgagcgc agcgagtcag tgagcgagga agcggaagag cgcccaatac gcaaaccgcc      4500
tctccccgcg cgttggccga ttcattaatg cagcagctgc gcgctcgctc gctcactgag      4560
gccgcccggg caaagcccgg gcgtcgggcg acctttggtc gcccggcctc agtgagcgag      4620
cgagcgcgca gagagggagt ggccaactcc atcactaggg gttccttgta gttaatgatt      4680
aacccgccat gctacttatc tacgtagcca tgctctagga cattgattat tgactagtgg      4740
agttccgcgt tacataactt acggtaaatg gcccgcctgg ctgaccgccc aacgacccccc     4800
gcccattgac gtcaataatg acgtatgttc ccatagtaac gccaataggg actttccatt      4860
gacgtcaatg ggtggagtat ttacggtaaa ctgcccactt ggcagtacat caagtgtatc      4920
atatgccaag tacgcccccct attgacgtca atgacggtaa atggcccgcc tggcattatg      4980
cccagtacat gaccttatgg gactttccta cttggcagta catctacgta ttagtcatcg     5040
ctattaccat ggtcgaggtg agccccacgt tctgcttcac tctccccatc tcccccccct     5100
```

-continued

```
ccccacccccc aattttgtat ttatttattt tttaattatt ttgtgcagcg atggggcgg   5160
gggggggggg gggcgcgcgc caggcggggc ggggcggggc gagggcgggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
ttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctggag   5940
cattagcaat gcgaacagaa gttttggcct ctgactgact tctgttcgtt gctaatgctc   6000
caggacacaa ggcctgttac tagcactcac atggaacaaa tggcctctag cctggaggct   6060
tgctgaaggc tgtatgctga aacataatgg attcagcagc gcgttttggc ctctgactga   6120
cgcgctgctg accattatgt ttcaggacac aaggcctgtt actagcactc acatggaaca   6180
aatggcctct agcctggagg cttgctgaag gctgtatgct gttatctttg cgaagctgcc   6240
atccgttttg gcctctgact gacggatggc agccgcaaag ataacaggac acaaggcctg   6300
ttactagcac tcacatggaa caaatggcct ctctagaat                          6339
```

SEQ ID NO: 21          moltype = DNA  length = 6337
FEATURE             Location/Qualifiers
source             1..6337
                    mol_type = other DNA
                    organism = synthetic construct
SEQUENCE: 21

```
aatcaacctc tggattacaa aatttgtgaa agattgactg gtattcttaa ctatgttgct   60
cctttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc cctttgggcc g cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgtttattact aatcaaagaa acggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata aggtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga caataacc   2640
ctgataaatg cttcaataat attgaaaaag gaagagtatg agtattcaac atttccgtgt   2700
cgcccttatt ccctttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
```

-continued

```
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctcacg acgggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc ttttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagatacctac agcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gcctttttgc ggcctttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcgggg caaagcccgg gcgtcgggcg acctttgtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccccc   5100
ccccaccccc aattttgtat ttatttattt tttaattatt ttgtgcagcg atggggggg   5160
ggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcggggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg cgagcgctg ccacgtcaga cgaagggcgc agcgagcgtc   5520
ctgatccttc cgcccggacg ctcaggacag cggcccgctg ctcataagac tcggccttag   5580
aacccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgtttc   5760
ttttttttc tacaggtcct gggtgacgaa cagggtaccg ccaccatggc caccggctct   5820
cgcacaagcc tgctgctggc tttcggactg ctgtgcctga cttggcctca ggaggctcca   5880
gccgctagca tcgataccgt cgctatgtgc tggaggcttg ctgaaggctg tatgctggct   5940
cctccacttg gtggtttggt tttggcctct gactgacgcg gcaacattct ggtgattaca   6000
ggacacaagc cctgttacta gcactcacat ggaacaaatg gcctctagcc tggaggcttg   6060
ctgaaggctg tatgctgtca taatcgctat ttggtgacgg gttttggcct tgactactacg   6120
ccgcaccaaa gcgattatga caggacacaa ggcctgttac tagcactcac atggaacaaa   6180
tggcctctag cctggaggct tgctgaaggc tgtatgctgt tctgatcctg aagttcgggt   6240
tcgttttggc ctctgactga cgaacccgaa ccaggatcag aacaggacac aaggcctgtt   6300
actagcactc acatggaaca aatggcctct ctagaat                            6337
```

```
SEQ ID NO: 22            moltype = DNA  length = 6339
FEATURE                  Location/Qualifiers
source                   1..6339
                         mol_type = other DNA
                         organism = synthetic construct
SEQUENCE: 22
aatcaacctc tggattacaa aatttgtgaa agattgactg gtattcttaa ctatgttgct    60
cctttacgc tatgtggata cgctgcttta atgcctttgt atcatgctat tgcttcccgt    120
atggctttca ttttctcctc cttgtataaa tcctggttgc tgtctctta tgaggagttg    180
tggcccgttg tcaggcaacg tggcgtggtg tgcactgtgt ttgctgacgc aacccccact    240
ggttggggca ttgccaccac ctgtcagctc ctttccggga ctttcgcttt ccccctccct    300
attgccacgg cggaactcat cgccgcctgc cttgcccgct gctggacagg ggctcggctg    360
ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgcc taagcttatc    600
gataccgtcg agatctaact tgtttattgc agcttataat ggttacaaat aaagcaatag    660
catcacaaat ttcacaaata aagcattttt ttcactgcat tctagttgtg gtttgtccaa    720
actcatcaat gtatcttatc atgtctggat ctcgacctcg actagagcat ggctacgtag    780
ataagtagca tggcgggtta tcattaact acaaggaacc cctagtgatg gagttggcca    840
ctccctctct gcgcgctcgc tcgctcactg aggccgggcg accaaaggtc gcccgacgcc    900
cgggctttgc ccgggcggcc tcagtgagcg agcgagcgcg cagctggcgt aatagcgaag    960
aggcccgcac cgatcgccct tcccaacagt tgcgcagcct gaatggcgaa tggcgattcc    1020
```

-continued

```
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tccttctcg ccacgttcgc    1440
cggctttccc cgtcaagctc taaatcgggg gctcccttta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta caggggtcata atgttttttgg tacaaccgat  2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctattttat aggttaatgt     2520
catgataata atggtttctt agacgtcagg tggcacttt cggggaaatg tgcgcggaac     2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
tttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc ttttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttt    4320
acggttcctg gccttttgct ggccttttgc tcacatgttc tttcctgcgt tatccctga    4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgga   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc     4800
gcccattgac gtcaataatg acgtatgttc ccatagtaac gccataaggt acttacccatt  4860
gacgtcaatg ggtggagtat ttacggtaaa ctgcccactt ggcagtacat caagtgtatc   4920
atatgccaag tacgcccct attgacgtca atgacggtaa atggcccgcc tggcattatg     4980
cccagtacat gaccttatgg gactttccta cttggcagta catctacgta ttagtcatcg   5040
ctattaccat ggtcgaggtg agccccacgt tctgcttcac tctccccatc tcccccccc    5100
cccacccccc aatttttgtat ttatttattt ttgtgcagcg atgggggcgg   5160
ggggggggg gggcgcgcgc caggcggggc ggggcggggc gaggggcggg gcggggcgag    5220
gcggagaggc gcggcggcag ccaatcagag cggcgcgctc cgaaagtttc cttttatggc   5280
gaggcggcgg cggcggcggc cctataaaaa gcgaagcgcg cggcggggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ggccgctccc   5460
cgggcgcccc cctcctcacg gcgagcgctg ccagtcagga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgtttc     5760
```

```
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgaaa   5940
tcttccggtg gttccactgc gttttggcct ctgactgacg cagtggaacc cggaagattt   6000
caggacacaa ggcctgttac tagcactcac atggaacaaa tggcctctag cctggaggct   6060
tgctgaaggc tgtatgctga tatcctgaat atggtatgca gcgttttggc ctctgactga   6120
cgctgcatac cattcaggat atcaggacac aaggcctgtt actagcactc acatggaaca   6180
aatggcctct agcctggagg cttgctgaag gctgtatgct gtttaaagct caaacgcgtt   6240
cgccgttttg gcctctgact gacggcgaac gcgtgagctt taaacaggac acaaggcctg   6300
ttactagcac tcacatggaa caaatggcct ctctagaat                         6339
```

SEQ ID NO: 23             moltype = DNA   length = 6339
FEATURE                   Location/Qualifiers
source                    1..6339
                          mol_type = other DNA
                          organism = synthetic construct
SEQUENCE: 23
```
aatcaacctc tggattacaa aatttgtgaa agattgactg gtattcttaa ctatgttgct   60
cctttacgc tatgtggata cgctgcttta atgcctttgt atcatgctat tgcttcccgt    120
atggctttca ttttctcctc cttgtataaa tcctggttgc tgtctcttta tgaggagttg   180
tggcccgttg tcaggcaacg tggcgtggtg tgcactgtgt ttgctgacgc aaccCCCcact  240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctcCCCgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggc taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg ctccctttaa gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgtttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
```

-continued

```
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggccttttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctga gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
ccccaccccc aattttgtat ttatttattt tttaattatt ttgtgcagcg atggggcgg   5160
ggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttctttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatgtc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtaa   5940
taaaggtctg ggaatcaccc gttttggcct ctgactgacg ggtgattccg acctttatta   6000
caggacacaa ggcctgttac tagcactcac atggaacaaa tggcctctag cctggaggct   6060
tgctgaaggc tgtatgctgt aatacgccag atcaccatca gcgttttggc ctctgactga   6120
cgctgatggt gctggcgtat tacaggacac aaggcctgtt actagcactc acatggaaca   6180
aatggcctct agcctggagg cttgctgaag gctgtatgct gatacagaaa cgaaggttca   6240
ggccgttttg gcctctgact gacggcctga acccgtttct gtatcaggac acaaggcctg   6300
ttactagcac tcacatggaa caaatggcct ctctagaat                           6339
```

SEQ ID NO: 24       moltype = DNA  length = 6339
FEATURE             Location/Qualifiers
source               1..6339
                      mol_type = other DNA
                      organism = synthetic construct
SEQUENCE: 24

```
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccccact   240
ggttggggca ttgccaccac ctgtcagctc ctttccggga ctttcgcttt ccccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg atagagctag cctgctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggct taccgttcct gtctaaaatc cctttaatcg gcctcctgtt tagctcccgc   1260
tctgattcta acgaggaaag cacgttatac gtgctcgtca aagcaaccat agtacgcgc   1320
ctgtagcggc gcattaagcg cggcgggtgt ggtggttacg cgcagcgtga ccgctacact   1380
tgccagcggc ctagcgcccg ctcctttcgc tttcttccct tccttttctcg ccacgttcgc   1440
cggctttccc cgtcaagctc taaatcgggg ctccctttta gggttccgat ttagtgcttt   1500
acggcacctc gaccccaaaa aacttgatta gggtgatggt tcacgtagtg gccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
```

-continued

```
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaattttta tccttgcgtt   2100
gaaataaagg cttctcccgc aaaagtatta cagggtcata atgttttttgg tacaaccgat   2160
ttagctttat gctctgaggc tttattgctt aattttgcta attctttgcc ttgcctgtat   2220
gatttattgg atgttggaat tcctgatgcg gtattttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcactttt cggggaaatg tgcgcggaac   2580
ccctatttgt ttatttttct aaatacattc aaatatgtat ccgctcatga gacaataacc   2640
ctgataaatg cttcaataat attgaaaaag gaagagtatg agtattcaac atttccgtgt   2700
cgcccttatt ccctttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta gcagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac cctctgactt gagcgtcgat   4260
tttgtgatgc tcgtcagggg ggcggagcct atggaaaaac gccagcaacg cggcctttt   4320
acggttcctg gccttttgct ggccttttgc tcacatgttc tttcctgcgt tatcccctga   4380
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcct   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagaggagt ggccaactcc atcactaggg gttccttgta gttaatgatt   4680
aacccgccat gctacttatc tacgtagcca tgctctagga cattgattat tgactagttt   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgccccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tccccccct   5100
ccccacccc aattttgtat ttatttattt tttaattatt ttgtgcagcg atggggggcgg   5160
ggggggggg gggcgcgcgc caggcggggc ggggcggggc gaggggcggg gcggggcgag   5220
gcggagaggt gcggcgcag ccaatcagag cggcggcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga caagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttcttttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgtca   5940
gatcgctgtg gtaaacaggc gttttggcct ctgactgacg cctgtttacc agcgatctga   6000
caggacacaa ggcctgttac tagcactcac atggaacaaa tggcctctag cctggaggct   6060
tgctgaagga gtgtatgctga gaatcagatc agatagcgat ccgttttggc ctctgactga   6120
cggatcgcta tctgctgatt ctcaggcacg aaggcctgtt actagcactc acatggaaca   6180
aatgccctct agcctggagg cttgctgaag gctgtatgct gaaacatgcc aacagcagaa   6240
tgccgttttg gcctctgact gacggcattc tgctgggcat gtttcaggac acaaggcctg   6300
ttactagcac tcacatggaa caaatggcct ctctagaat                          6339
```

-continued

```
SEQ ID NO: 25              moltype = DNA   length = 6339
FEATURE                    Location/Qualifiers
source                     1..6339
                           mol_type = other DNA
                           organism = synthetic construct
SEQUENCE: 25
aatcaacctc tggattacaa aatttgtgaa agattgactg gtattcttaa ctatgttgct   60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aacccccact   240
ggttggggca ttgccaccac ctgtcagctc ctttccggga ctttcgcttt cccctccct   300
attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgcc taagcttatc   600
gataccgtcg agatctaact tgtttattgc agcttataat ggttacaaat aaagcaatag   660
catcacaaat ttcacaaata aagcattttt ttcactgcat tctagttgtg gtttgtccaa   720
actcatcaat gtatcttatc atgtctggat ctcgacctcg actagagcat ggctacgtag   780
ataagtagca tggcgggtta atcattaact acaaggaacc cctagtgatg gagttggcca   840
ctccctctct gcgcgctcgc tcgctcactg aggccgggcg accaaaggtc gcccgacgcc   900
cgggctttgc ccgggcggcc tcagtgagcg agcgagcgcg cagctggcgt aatagcgaag   960
aggcccgcac cgatcgccct tcccaacagt tgcgcagcct gaatggcgaa tggcgattcc   1020
gttgcaatgg ctggcggtaa tattgttctg gatattacca gcaaggccga tagtttgagt   1080
tcttctactc aggcaagtga tgttattact aatcaaagaa gtattgcgac aacggttaat   1140
ttgcgtgatg gacagactct tttactcggt ggcctcactg attataaaaa cacttctcag   1200
gattctggcg taccgttcct gtctaaaatc cctttaatcg gcctcctgtt tagctcccgc   1260
tctgattcta acgaggaaag cacgttatac gtgctcgtca aagcaaccat agtacgcgcc   1320
ctgtagcggc gcattaagcg cggcgggtgt ggtggttacg cgcagcgtga ccgctacact   1380
tgccagcgcc ctagcgcccg ctcctttcgc tttcttccct tcctttctcg ccacgttcgc   1440
cggctttccc cgtcaagctc taaatcgggg gctccctta gggttccgat ttagtgcttt   1500
acggcacctc gaccccaaaa aacttgatta gggtgatggt tcacgtagtg ggccatcgcc   1560
ctgatagacg gtttttcgcc ctttgacgtt ggagtccacg ttctttaata gtggactctt   1620
gttccaaact ggaacaacac tcaaccctat ctcggtctat tcttttgatt tataagggat   1680
tttgccgatt tcggcctatt ggttaaaaaa tgagctgatt taacaaaaat ttaacgcgaa   1740
ttttaacaaa atattaacgt ttacaattta aatatttgct tatacaatct tcctgttttt   1800
ggggcttttc tgattatcaa ccggggtaca tatgattgac atgctagttt tacgattacc   1860
gttcatcgat tctcttgttt gctccagact ctcaggcaat gacctgatag cctttgtaga   1920
gacctctcaa aaatagctac cctctccggc atgaatttat cagctagaac ggttgaatat   1980
catattgatg gtgatttgac tgtctccggc ctttctcacc cgtttgaatc tttacctaca   2040
cattactcag gcattgcatt taaaatatat gagggttcta aaaatttta tccttgcgtt   2100
gaaataaagg cttctcccgc aaaagtatta cagggtcata atgtttttgg tacaaccgat   2160
ttagctttat gctctgaggc tttattgctt aattttgcc ttgcctgtat   2220
gatttattgg atgttggaat tcctgatgcg gtatttttctc cttacgcatc tgtgcggtat   2280
ttcacaccgc atatggtgca ctctcagtac aatctgctct gatgccgcat agttaagcca   2340
gccccgacac ccgccaacac ccgctgacgc gccctgacgg gcttgtctgc tcccggcatc   2400
cgcttacaga caagctgtga ccgtctccgg gagctgcatg tgtcagaggt tttcaccgtc   2460
atcaccgaaa cgcgcgagac gaaagggcct cgtgatacgc ctatttttat aggttaatgt   2520
catgataata atggtttctt agacgtcagg tggcacttttt cggggaaatg tgcgcggaac   2580
ccctatttgt ttatttttct aaatacattc aaatatgtat ccgctcatga caataacc   2640
ctgataaatg cttcaataat attgaaaaag gaagagtatg agtattcaac atttccgtgt   2700
cgcccttatt cccttttttg cggcattttg ccttcctgtt tttgctcacc cagaaacgct   2760
ggtgaaagta aaagatgctg aagatcagtt gggtgcacga gtgggttaca tcgaactgga   2820
tctcaacagc ggtaagatcc ttgagagttt tcgccccgaa gaacgttttc caatgatgag   2880
cacttttaaa gttctgctat gtggcgcggt attatcccgt attgacgccg ggcaagagca   2940
actcggtcgc cgcatacact attctcagaa tgacttggtt gagtactcac cagtcacaga   3000
aaagcatctt acggatggca tgacagtaag agaattatgc agtgctgcca taaccatgag   3060
tgataacact gcggccaact tacttctgac aacgatcgga ggaccgaagg agctaaccgc   3120
ttttttgcac aacatggggg atcatgtaac tcgccttgat cgttgggaac cggagctgaa   3180
tgaagccata ccaaacgacg agcgtgacac cacgatgcct gtagcaatgg caacaacgtt   3240
gcgcaaacta ttaactggcg aactacttac tctagcttcc cggcaacaat taatagactg   3300
gatggaggcg gataaagttg caggaccact tctgcgctcg gcccttccgg ctggctggtt   3360
tattgctgat aaatctggag ccggtgagcg tgggtctcgc ggtatcattg cagcactggg   3420
gccagatggt aagccctccc gtatcgtagt tatctacacg acggggagtc aggcaactat   3480
ggatgaacga aatagacaga tcgctgagat aggtgcctca ctgattaagc attggtaact   3540
gtcagaccaa gtttactcat atatacttta gattgattta aaacttcatt tttaatttaa   3600
aaggatctag gtgaagatcc tttttgataa tctcatgacc aaaatccctt aacgtgagtt   3660
ttcgttccac tgagcgtcag accccgtaga aaagatcaaa ggatcttctt gagatccttt   3720
ttttctgcgc gtaatctgct gcttgcaaac aaaaaaacca ccgctaccag cggtggtttg   3780
tttgccggat caagagctac caactctttt tccgaaggta actggcttca gcagagcgca   3840
gataccaaat actgtccttc tagtgtagcc gtagttaggc caccacttca agaactctgt   3900
agcaccgcct acatacctcg ctctgctaat cctgttacca gtggctgctg ccagtggcga   3960
taagtcgtgt cttaccgggt tggactcaag acgatagtta ccggataagg cgcagcggtc   4020
gggctgaacg gggggttcgt gcacacagcc cagcttggag cgaacgacct acaccgaact   4080
gagataccta cagcgtgagc tatgagaaag cgccacgctt cccgaaggga gaaaggcgga   4140
caggtatccg gtaagcggca gggtcggaac aggagagcgc acgagggagc ttccaggggg   4200
aaacgcctgg tatctttata gtcctgtcgg gtttcgccac ctctgacttg agcgtcgatt   4260
tttgtgatgc tcgtcagggg ggcggagcct atggaaaaac gccagcaacg cggcctttttt   4320
acggttcctg gccttttgct ggccttttgc tcacatgttc tttcctgcgt tatccctga   4380
```

-continued

```
ttctgtggat aaccgtatta ccgcctttga gtgagctgat accgctcgcc gcagccgaac   4440
gaccgagcgc agcgagtcag tgagcgagga agcggaagag cgcccaatac gcaaaccgcc   4500
tctccccgcg cgttggccga ttcattaatg cagcagctgc gcgctcgctc gctcactgag   4560
gccgcccggg caaagcccgg gcgtcgggcg acctttggtc gcccggcctc agtgagcgag   4620
cgagcgcgca gagagggagt ggccaactcc atcactaggg gttccttgta gttaatgatt   4680
aacccgccat gctacttatc tacgtagcca tgctctagga cattgattat tgactagtgg   4740
agttccgcgt tacataactt acggtaaatg gcccgcctgg ctgaccgccc aacgacccc   4800
gcccattgac gtcaataatg acgtatgttc ccatagtaac gccaataggg actttccatt   4860
gacgtcaatg ggtggagtat ttacggtaaa ctgcccactt ggcagtacat caagtgtatc   4920
atatgccaag tacgcccct attgacgtca atgacggtaa atggcccgcc tggcattatg   4980
cccagtacat gaccttatgg gactttccta cttggcagta catctacgta ttagtcatcg   5040
ctattaccat ggtcgaggtg agccccacgt tctgcttcac tctccccatc tcccccccct   5100
ccccacccc aattttgtat ttatttattt tttaattatt ttgtgcagcg atgggggcgg   5160
ggggggggg gggcgcgcgc caggcggggc ggggcggggc gaggggcggg gcggggcgag   5220
gcggagaggt gcggcggcag ccaatcagag cggcgcgctc cgaaagtttc cttttatggc   5280
gaggcggcgg cggcggcggc cctataaaaa gcgaagcgcg cggcgggcgg gagtcgctgc   5340
gcgctgcctt cgccccgtgc cccgctccgc cgccgcctcg cgccgcccgc cccggctctg   5400
actgaccgcg ttactaaaac aggtaagtcc ggcctccgcg ccgggttttg gcgcctcccg   5460
cgggcgcccc cctcctcacg gcgagcgctg ccacgtcaga cgaagggcgc agcgagcgtc   5520
ctgatccttc cgcccggacg ctcaggacag cggcccgctg ctcataagac tcggccttag   5580
aaccccagta tcagcagaag gacattttag gacgggactt gggtgactct agggcactgg   5640
ttttcttttcc agagagcgga acaggcgagg aaaagtagtc ccttctcggc gattctgcgg   5700
agggatctcc gtggggcggt gaacgccgat gatgcctcta ctaaccatgt tcatgttttc   5760
tttttttttc tacaggtcct gggtgacgaa cagggtaccg ccaccatggc caccggctct   5820
cgcacaagcc tgctgctggc tttcggactg ctgtgcctgc cttggctcca ggagggctcc   5880
gccgctagca tcgataccgt cgctatgtgc tggaggcttg ctgaaggctg tatgctgaca   5940
atcagatatg gttgctcggc gttttggcct ctgactgacg ccgagcaact atctgattgt   6000
caggacacaa ggcctgttac tagcactcac atggaacaaa tggcctctag cctgaggct   6060
tgctgaaggc tgtatgctgt ttcacaatgc atcgttcagc gcgttttggc ctctgactga   6120
cgcgctgaac ggcattgtga aacaggacac aaggcctgtt actagcactc acatggaaca   6180
aatggcctct agcctggagg cttgctgaag gctgtatgct gacaataatg ccaacagggt   6240
ggtcgttttg gcctctgact gacgaccacc ctggcatta ttgtcaggac acaaggcctg   6300
ttactagcac tcacatggaa caaatggcct ctctagaat                           6339
```

COMPOSITION FOR REGULATING PRODUCTION OF INTERFERING RIBONUCLEIC ACID

CROSS REFERENCE TO RELATED APPLICATION

The present application is a continuation of U.S. patent application Ser. No. 18/968,602 filed Dec. 4, 2024, entitled "COMPOSITION FOR REGULATING PRODUCTION OF INTERFERING RIBONUCLEIC ACID" currently pending, which is a division of U.S. patent application Ser. No. 18/582,272 filed Feb. 20, 2024, entitled "COMPOSITION FOR REGULATING PRODUCTION OF INTERFERING RIBONUCLEIC ACID" currently pending, the entirety of which are incorporated herein by reference.

SEQUENCE LISTING

This application contains a Sequence Listing electronically submitted via Patent Center to the United States Patent and Trademark Office as an XML Document file entitled "A8149441US-Sequence Listing.xml" created on 2024 Feb. 12 and having a size of 110,545 bytes. The information contained in the Sequence Listing is incorporated by reference herein.

TECHNICAL FIELD

The present disclosure generally relates to compositions for regulating production of interfering ribonucleic acid (RNA). In particular, the present disclosure relates to compositions for regulating gene expression and therefore, the production of interfering RNA, that will suppress serotonin receptor expression.

BACKGROUND

Bioactive molecules, including complements and factors, are necessary for the homeostatic control of biological systems.

When bioactive molecules are over-expressed, under-expressed or mis-expressed, homeostasis is lost, and disease is often the result.

As such, it may be desirable to establish therapies, treatments and/or interventions that address when homeostasis and regulation of bioactive molecules is lost to prevent or treat the resulting disease.

SUMMARY

Some embodiments of the present disclosure relate to one or more compositions that upregulate the production of one or more sequences of micro-interfering ribonucleic acid (miRNA). The sequences of miRNA may be complementary to a sequence of target messenger RNA (mRNA) that encodes for translation of a target biomolecule and the miRNA can cause the target mRNA to be degraded or inactivated, thereby causing a decrease in bioavailability of the target biomolecule because it is degraded or inactivated by the miRNA, thereby decreasing the bioavailability of the target biomolecule within a subject that is administered the one or more compositions. In some embodiments of the present disclosure, the target biomolecule is a serotonin receptor. In some embodiments of the present disclosure, the target biomolecule is a serotonin receptor such as serotonin receptor 5HT1a. In some embodiments of the present disclosure, the target biomolecule is a serotonin receptor such as serotonin receptor 5HT1b. In some embodiments of the present disclosure, the target biomolecule is a serotonin receptor such as serotonin receptor 5HT1c. In some embodiments of the present disclosure, the target biomolecule is a serotonin receptor such as serotonin receptor 5HT1d. In some embodiments of the present disclosure, the target biomolecule is a serotonin receptor such as serotonin receptor 5HT1e. In some embodiments of the present disclosure, the target biomolecule is a serotonin receptor such as serotonin receptor 5HT1f. In some embodiments of the present disclosure, the target biomolecule is a serotonin receptor such as serotonin receptor 5HT2a. In some embodiments of the present disclosure, the target biomolecule is a serotonin receptor such as serotonin receptor 5HT2b. In some embodiments of the present disclosure, the target biomolecule is a serotonin receptor such as serotonin receptor 5HT2c. In some embodiments of the present disclosure, the target biomolecule is a serotonin receptor such as serotonin receptor 5HT3. In some embodiments of the present disclosure, the target biomolecule is a serotonin receptor such as serotonin receptor 5HT4. In some embodiments of the present disclosure, the target biomolecule is a serotonin receptor such as serotonin receptor 5HT6. In some embodiments of the present disclosure, the target biomolecule is a serotonin receptor such as serotonin receptor 5HT7.

In some embodiments of the present disclosure the compositions comprise a plasmid of deoxyribonucleic acid (DNA) that includes one or more insert sequences of nucleic acids that encode for the production of miRNA and a backbone sequence of nucleic acids that facilitates introduction of the one or more insert sequences into one or more of a subject's cells where it is expressed and/or replicated. Expression of the one or more insert sequences by one or more cells of the subject results in an increased production of the miRNA and, therefore, decreased translation or production of the target biomolecule by one or more of the subject's cells.

Some embodiments of the present disclosure relate to compositions that upregulate the production of miRNA that degrades, or causes degradation of, or inactivates or causes the inactivation of, the target mRNA of the target biomolecule.

Some embodiments of the present disclosure relate to a recombinant plasmid (RP). In some embodiments of the present disclosure, the RP comprises a nucleotide sequence of SEQ ID NO. 1 and SEQ ID NO. 2. The RP comprises a nucleotide sequence encoding one or more nucleotide sequences encoding a miRNA sequence that targets the mRNA of serotonin receptor 5HT1a.

Some embodiments of the present disclosure relate to a recombinant plasmid. In some embodiments of the present disclosure, the RP comprises a nucleotide sequence of SEQ ID NO. 1 and SEQ ID NO. 3. The RP comprises a nucleotide sequence encoding one or more nucleotide sequences encoding a miRNA sequence that targets the mRNA of serotonin receptor 5HT1b.

Some embodiments of the present disclosure relate to a recombinant plasmid. In some embodiments of the present disclosure, the RP comprises a nucleotide sequence of SEQ ID NO. 1 and SEQ ID NO. 4. The RP comprises a nucleotide sequence encoding one or more nucleotide sequences encoding a miRNA sequence that targets the mRNA of serotonin receptor 5HT1d.

Some embodiments of the present disclosure relate to a recombinant plasmid. In some embodiments of the present disclosure, the RP comprises a nucleotide sequence of SEQ ID NO. 1 and SEQ ID NO. 5. The RP comprises a nucleotide sequence encoding one or more nucleotide sequences encoding a miRNA sequence that targets the mRNA of serotonin receptor 5HT1e.

Some embodiments of the present disclosure relate to a recombinant plasmid. In some embodiments of the present disclosure, the RP comprises a nucleotide sequence of SEQ ID NO. 1 and SEQ ID NO. 6. The RP comprises a nucleotide sequence encoding one or more nucleotide sequences encoding a miRNA sequence that targets the mRNA of serotonin receptor 5HT1f.

Some embodiments of the present disclosure relate to a recombinant plasmid. In some embodiments of the present disclosure, the RP comprises a nucleotide sequence of SEQ ID NO. 1 and SEQ ID NO. 7. The RP comprises a nucleotide sequence encoding one or more nucleotide sequences encoding a miRNA sequence that targets the mRNA of serotonin receptor 5HT2a.

Some embodiments of the present disclosure relate to a recombinant plasmid. In some embodiments of the present disclosure, the RP comprises a nucleotide sequence of SEQ ID NO. 1 and SEQ ID NO. 8. The RP comprises a nucleotide sequence encoding one or more nucleotide sequences encoding a miRNA sequence that targets the mRNA of serotonin receptor 5HT2b.

Some embodiments of the present disclosure relate to a recombinant plasmid. In some embodiments of the present disclosure, the RP comprises a nucleotide sequence of SEQ ID NO. 1 and SEQ ID NO. 9. The RP comprises a nucleotide sequence encoding one or more nucleotide sequences encoding a miRNA sequence that targets the mRNA of serotonin receptor 5HT2c.

Some embodiments of the present disclosure relate to a recombinant plasmid. In some embodiments of the present disclosure, the RP comprises a nucleotide sequence of SEQ ID NO. 1 and SEQ ID NO. 10. The RP comprises a nucleotide sequence encoding one or more nucleotide sequences encoding a miRNA sequence that targets the mRNA of serotonin receptor 5HT3.

Some embodiments of the present disclosure relate to a recombinant plasmid. In some embodiments of the present disclosure, the RP comprises a nucleotide sequence of SEQ ID NO. 1 and SEQ ID NO. 11. The RP comprises a nucleotide sequence encoding one or more nucleotide sequences encoding a miRNA sequence that targets the mRNA of serotonin receptor 5HT4.

Some embodiments of the present disclosure relate to a recombinant plasmid. In some embodiments of the present disclosure, the RP comprises a nucleotide sequence of SEQ ID NO. 1 and SEQ ID NO. 12. The RP comprises a nucleotide sequence encoding one or more nucleotide sequences encoding a miRNA sequence that targets the mRNA of serotonin receptor 5HT6.

Some embodiments of the present disclosure relate to a recombinant plasmid. In some embodiments of the present disclosure, the RP comprises a nucleotide sequence of SEQ ID NO. 1 and SEQ ID NO. 13 The RP comprises a nucleotide sequence encoding one or more nucleotide sequences encoding a miRNA sequence that targets the mRNA of serotonin receptor 5HT7.

Some embodiments of the present disclosure relate to a method of making a composition/target cell complex. The method comprising a step of administering a RP comprising SEQ ID NO. 1 and one of SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, or SEQ ID NO. 13 to a target cell for forming the composition/target cell complex, wherein the composition/target cell complex causes the target cell to increase production of one or more sequences of miRNA that decreases production of a target biomolecule.

Embodiments of the present disclosure relate to at least one approach for inducing endogenous production of one or more sequences of miRNA that target and silence the mRNA of a target biomolecule, for example serotonin receptor 5HT1a. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1a, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1b. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1b, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1d. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1d, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1e. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1e, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT1f. A first approach utilizes gene vectors containing nucleotide sequences for increasing the endogenous production of one or more sequences of miRNA, which are complete or partial sequences and/or combinations thereof, that target and silence the mRNA of serotonin receptor 5HT1f, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2a. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2a, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2b. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2b, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT2c. A first approach utilizes gene vectors containing nucleotide sequences for increasing the endogenous production of one or more sequences of miRNA, which are complete or partial sequences and/or combinations thereof, that target and silence the mRNA of serotonin receptor 5HT2c, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT3. A first approach utilizes gene vectors containing nucleotide sequences for increasing the endogenous production of one or more sequences of miRNA, which are complete or partial sequences and/or combinations thereof, that target and silence the mRNA of serotonin receptor 5HT3 which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT4 A first approach utilizes gene vectors containing nucleotide sequences for increasing the endogenous production of one or more sequences of miRNA, which are complete or partial sequences and/or combinations thereof, that target and silence the mRNA of serotonin receptor 5HT4, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT6. A first approach utilizes gene vectors containing nucleotide sequences for increasing the endogenous production of one or more sequences of miRNA, which are complete or partial sequences and/or combinations thereof, that target and silence the mRNA of serotonin receptor 5HT6, which can be administered to a subject to increase the subject's production of one or more sequences of the miRNA.

Embodiments of the present disclosure relate to at least one approach for inducing endogenous production of one or more sequences of miRNA that target and silence the mRNA of a target biomolecule, for example serotonin receptor 5HT7. A first approach utilizes gene vectors containing nucleotide sequences for increasing the endogenous production of one or more sequences of miRNA, which are complete or partial sequences and/or combinations thereof, that target and silence the mRNA of serotonin receptor 5HT7, which can be administered to a subject to increase the subject's production of one or more sequences of the miRNA.

DETAILED DESCRIPTION

Unless defined otherwise, all technical and scientific terms used therein have the meanings that would be commonly understood by one of skill in the art in the context of the present description. Although any methods and materials similar or equivalent to those described therein can also be used in the practice or testing of the present disclosure, the preferred methods and materials are now described. All publications mentioned therein are incorporated therein by reference to disclose and describe the methods and/or materials in connection with which the publications are cited.

As used therein, the singular forms "a", "an", and "the" include plural references unless the context clearly dictates otherwise. For example, reference to "a composition" includes one or more compositions and reference to "a subject" or "the subject" includes one or more subjects.

As used therein, the terms "about" or "approximately" refer to within about 25%, preferably within about 20%, preferably within about 15%, preferably within about 10%, preferably within about 5% of a given value or range. It is understood that such a variation is always included in any given value provided therein, whether or not it is specifically referred to.

As used therein, the term "ameliorate" refers to improve and/or to make better and/or to make more satisfactory.

As used therein, the term "cell" refers to a single cell as well as a plurality of cells or a population of the same cell type or different cell types. Administering a composition to a cell includes in vivo, in vitro and ex vivo administrations and/or combinations thereof.

As used therein, the term "complex" refers to an association, either direct or indirect, between one or more particles of a composition and one or more target cells. This association results in a change in the metabolism of the target cell. As used therein, the phrase "change in metabolism" refers to an increase or a decrease in the one or more target cells' production of one or more proteins, and/or any post-translational modifications of one or more proteins.

As used therein, the term "composition" refers to a substance that, when administered to a subject, causes one or more chemical reactions and/or one or more physical reactions and/or one or more physiological reactions and/or one or more biological reactions in the subject. In some embodiments of the present disclosure, the composition is a plasmid vector.

As used therein, the term "endogenous" refers to the production and/or modification of a molecule that originates within a subject.

As used therein, the term "exogenous" refers to a molecule that is within a subject but that did not originate within the subject. As used therein, the terms "production", "producing" and "produce" refer to the synthesis and/or replication of DNA, the transcription of one or more sequences of RNA, the translation of one or more amino acid sequences, the post-translational modifications of an amino acid sequence, and/or the production of one or more regulatory molecules that can influence the production and/or functionality of an effector molecule or an effector cell. For clarity, "production" is also used therein to refer to the functionality of a regulatory molecule, unless the context reasonably indicates otherwise.

As used therein, the term "subject" refers to any therapeutic target that receives the composition. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types, ex vivo preparations, and/or a sample of biological materials such as tissue, and/or biological fluids.

As used therein, the term "target biomolecule" refers to a serotonin receptor that is found within a subject. A biomolecule may be endogenous or exogenous to a subject and when bioavailable the biomolecule may inhibit or stimulate a biological process within the subject.

As used therein, the term "target cell" refers to one or more cells and/or cell types that are deleteriously affected, either directly or indirectly, by a dysregulated biomolecule. The term "target cell" also refers to cells that are not deleteriously affected but that are the cells in which it is desired that the composition interacts.

As used therein, the term "therapeutically effective amount" refers to the amount of the composition used that is of sufficient quantity to ameliorate, treat and/or inhibit one or more of a disease, disorder or a symptom thereof. The "therapeutically effective amount" will vary depending on the composition used, the route of administration of the composition and the severity of the disease, disorder or symptom thereof. The subject's age, weight and genetic make-up may also influence the amount of the composition that will be a therapeutically effective amount.

As used therein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment" refers to any treatment of a disease, disorder, or symptom thereof in a subject and includes: (a) preventing the disease from occurring in a subject which may be predisposed to the disease but has not yet been diagnosed as having it; (b) inhibiting the disease, i.e., arresting its development; and (c) ameliorating the disease.

As used therein, the terms "unit dosage form" and "unit dose" refer to a physically discrete unit that is suitable as a unitary dose for patients. Each unit contains a predetermined quantity of the composition and optionally, one or more suitable pharmaceutically acceptable carriers, one or more excipients, one or more additional active ingredients, or combinations thereof. The amount of composition within each unit is a therapeutically effective amount.

Where a range of values is provided therein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

In some embodiments of the present disclosure, a composition is a recombinant plasmid (RP) for introducing genetic material, such as one or more nucleotide sequences, into a target cell for reproduction or transcription of an insert that comprises one or more nucleotide sequences that are carried within the RP. In some embodiments of the present disclosure, the RP is delivered without a carrier, by a viral vector, by a protein coat, or by a lipid vesicle. In some embodiments of the present disclosure, the vector is an adeno-associated virus (AAV) vector.

In some embodiments of the present disclosure, the insert comprises one or more nucleotide sequences that encode for production of at least one sequence of miRNA that decreases the production of target biomolecules. The miRNA may, directly or indirectly, bind to and degrade the target mRNA or otherwise inactivate the target mRNA so that less or none of the target-biomolecule protein is produced.

In some embodiments of the present disclosure, the target biomolecule is serotonin receptor 5HT1a.

In some embodiments of the present disclosure, the target biomolecule is serotonin receptor 5HT1b.

In some embodiments of the present disclosure, the target biomolecule is serotonin receptor 5HT1d.

In some embodiments of the present disclosure, the target biomolecule is serotonin receptor 5HT1e.

In some embodiments of the present disclosure, the target biomolecule is serotonin receptor 5HT1f.

In some embodiments of the present disclosure, the target biomolecule is serotonin receptor 5HT2a.

In some embodiments of the present disclosure, the target biomolecule is serotonin receptor 5HT2b.

In some embodiments of the present disclosure, the target biomolecule is serotonin receptor 5HT2c.

In some embodiments of the present disclosure, the target biomolecule is serotonin receptor 5HT3.

In some embodiments of the present disclosure, the target biomolecule is serotonin receptor 5HT4.

In some embodiments of the present disclosure, the target biomolecule is serotonin receptor 5HT6.

In some embodiments of the present disclosure, the target biomolecule is serotonin receptor 5HT7.

In some embodiments of the present disclosure, the insert comprises one or more nucleotide sequences that each encode for one or more miRNA sequences that may be complementary to and degrade, or cause degradation of, mRNA of the target biomolecule.

Some embodiments of the present disclosure relate to a composition that can be administered to a subject with a condition that results, directly or indirectly, from the production of a dysregulated biomolecule. When a therapeutically effective amount of the composition is administered to the subject, the subject may change production and/or functionality of one or more biomolecules.

In some embodiments of the present disclosure, the subject may respond to receiving the therapeutic amount of the composition by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more biomolecules.

In some embodiments of the present disclosure, administering a therapeutic amount of the composition to a subject upregulates the production, functionality or both one or more sequences of miRNA that each target the mRNA of one or more target biomolecules. In some embodiments of the present disclosure, there are one, two, three, four, five, or six miRNA sequences that each are complementary to and degrade, or cause degradation of, one biomolecule, such as the mRNA of serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7. In some embodiments of the present disclosure, the composition may comprise multiple copies of the same nucleotide sequence of miRNA.

In some embodiments of the present disclosure, the composition is an RP that may be used for gene therapy. The gene therapy is useful for increasing the subject's endogenous production of one or more sequences of miRNA that target the mRNA of a target biomolecule. For example, the RP can contain one or more nucleotide sequences that cause increased production of one or more nucleotide sequences that cause an increased production of one or more miRNA sequences that are each complementary to and degrade, or cause degradation of, or inactivate, or cause inactivation of, one biomolecule, such as serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7.

In some embodiments of the present disclosure, the delivery vehicle of the RP used for gene therapy may be a vector that is comprised of a virus that can be enveloped, or not (unenveloped), replication effective or not (replication ineffective), or combinations thereof. In some embodiments of the present disclosure, the vector is a virus that is not enveloped and not replication effective. In some embodiments of the present disclosure, the vector is a virus of the Parvoviridae family. In some embodiments of the present disclosure, the vector is a virus of the genus *Dependoparvovirus*. In some embodiments of the present disclosure, the vector is an adeno-associated virus (AAV). In some embodiments of the present disclosure, the vector is a recombinant AAV. In some embodiments of the present disclosure, the vector is a recombinant AAV6.2FF.

In some embodiments of the present disclosure, the delivery vehicle of the RP used for gene therapy may be a protein coat.

In some embodiments of the present disclosure, the delivery vehicle of the RP used for gene therapy may be a lipid vesicle.

The embodiments of the present disclosure also relate to administering a therapeutically effective amount of the composition. In some embodiments of the present disclosure, the therapeutically effective amount of the composition that is administered to a patient is between about 10 and about $1 \times 10^{16}$ TCID$_{50}$/kg (50% tissue culture infective dose per kilogram of the patient's body mass). In some embodiments of the present disclosure, the therapeutically effective amount of the composition that is administered to the patient is about $1 \times 10^{13}$ TCID$_{50}$/kg. In some embodiments of the present disclosure, the therapeutically effective amount of the composition that is administered to a patient is measured in TPC/kg (total particle count of the composition per kilogram of the patient's body mass). In some embodiments the therapeutically effective amount of the composition is between about 10 and about $1 \times 10^{16}$ TCP/kg.

Some embodiments of the present disclosure relate to an adeno-associated virus (AAV) genome consisting of a RP that when operable inside a target cell will cause the target cell to produce a miRNA sequence that downregulates production of a biomolecule, with examples being serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7. The RP is comprised of AAV2 inverted terminal repeats (ITRs), a composite CASI promoter, a human growth hormone (HGH) signal peptide followed by a miRNA expression cassette containing up to six different miRNAs targeting the mRNA of serotonin receptor 5HT1a, serotonin receptor 5HT1b, serotonin receptor 5HT1d, serotonin receptor 5HT1e, serotonin receptor 5HT1f, serotonin receptor 5HT2a, serotonin receptor 5HT2b, serotonin receptor 5HT2c, serotonin receptor 5HT3, serotonin receptor 5HT4, serotonin receptor 5HT6, or serotonin receptor 5HT7, followed by a Woodchuck Hepatitis Virus post-transcriptional regulatory element (WPRE) and a Simian virus 40 (SV40) polyadenylation (polyA) signal.

```
(backbone sequence No. 1):
                                        SEQ ID NO. 1
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC
```

-continued

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

-continued

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

-continued

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

C 3'

(miRNA expression cassette No. 2-
serotonin receptor 5HT1a):
SEQ ID NO. 2
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGATCAATCGGA

TTGCGGTAATCGCGTTTTGGCCTCTGACTGACGCGATTACCGATCCGATT

GATCAGGACACAAGGCCTGTTACTAGCACTCACATGGAACAAATGGCCTC

TAGCCTGGAGGCTTGCTGAAGGCTGTATGCTGATCTTTGCTAAATTGGTG

CACGCGTTTTGGCCTCTGACTGACGCGTGCACCATTAGCAAAGATCAGGA

CACAAGGCCTGTTACTAGCACTCACATGGAACAAATGGCCTCTAGCCTGG

AGGCTTGCTGAAGGCTGTATGCTGACTTCAATCACAATTCCAGCGCCGTT

TTGGCCTCTGACTGACGGCGCTGGAAGTGATTGAAGTCAGGACACAAGGC

CTGTTACTAGCACTCACATGGAACAAATGGCCTCTCTAGAAT 3'

(miRNA expression cassette No. 3-
serotonin receptor 5HT1b):
SEQ ID NO. 3
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGTAATCTTTCG

CTGGCTGCAGTTCGTTTTGGCCTCTGACTGACGAACTGCAGCGCGAAAGA

TTACAGGACACAAGGCCTGTTACTAGCACTCACATGGAACAAATGGCCTC

TAGCCTGGAGGCTTGCTGAAGGCTGTATGCTGTGTTAATGCTGATGTCAC

GCTGCGTTTTGGCCTCTGACTGACGCAGCGTGACCAGCATTAACACAGGA

CACAAGGCCTGTTACTAGCACTCACATGGAACAAATGGCCTCTAGCCTGG

AGGCTTGCTGAAGGCTGTATGCTGTTCACCTGGTTAACACATACACCGTT

TTGGCCTCTGACTGACGGTGTATGTGAACCAGGTGAACAGGACACAAGGC

CTGTTACTAGCACTCACATGGAACAAATGGCCTCTCTAGAAT 3'

-continued (miRNA expression cassette No. 4-
serotonin receptor 5HT1d):
SEQ ID NO. 4
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGATTTCTTCCT

GTGCGCTTTCGCCGTTTTGGCCTCTGACTGACGGCGAAAGCGCAGGAAGA

AATCAGGACACAAGGCCTGTTACTAGCACTCACATGGAACAAATGGCCTC

TAGCCTGGAGGCTTGCTGAAGGCTGTATGCTGAGAATAATCAGATCAGCA

CGCTCGTTTTGGCCTCTGACTGACGAGCGTGCTGCTGATTATTCTCAGGA

CACAAGGCCTGTTACTAGCACTCACATGGAACAAATGGCCTCTAGCCTGG

AGGCTTGCTGAAGGCTGTATGCTGTAATCAGGCTGAATTCAGATAGCGTT

TTGGCCTCTGACTGACGCTATCTGAACAGCCTGATTACAGGACACAAGGC

CTGTTACTAGCACTCACATGGAACAAATGGCCTCTCTAGAAT 3'

(miRNA expression cassette No. 5-
serotonin receptor 5HT1e):
SEQ ID NO. 5
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGATAATCACCG

CTGCAGGTTCAGCGTTTTGGCCTCTGACTGACGCTGAACCTGGCGGTGAT

TATCAGGACACAAGGCCTGTTACTAGCACTCACATGGAACAAATGGCCTC

TAGCCTGGAGGCTTGCTGAAGGCTGTATGCTGTTCAATCGCGTATTGGTA

ATCGCGTTTTGGCCTCTGACTGACGCGATTACCAACGCGATTGAACAGGA

CACAAGGCCTGTTACTAGCACTCACATGGAACAAATGGCCTCTAGCCTGG

AGGCTTGCTGAAGGCTGTATGCTGTGATCATGCTGAAAATGGTGCACGTT

TTGGCCTCTGACTGACGTGCACCATTCAGCATGATCACAGGACACAAGGC

CTGTTACTAGCACTCACATGGAACAAATGGCCTCTCTAGAAT 3'

(miRNA expression cassette No. 6-
serotonin receptor 5HT1f):
SEQ ID NO. 6
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGAGGTAATATC

CTGACGCTCAGCCGTTTTGGCCTCTGACTGACGGCTGAGCGTGGATATTA

CCTCAGGACACAAGGCCTGTTACTAGCACTCACATGGAACAAATGGCCTC

TAGCCTGGAGGCTTGCTGAAGGCTGTATGCTGTACAGAATCAGATAATCA

GCGCCGTTTTGGCCTCTGACTGACGGCGCTGATTCTGATTCTGTACAGGA

CACAAGGCCTGTTACTAGCACTCACATGGAACAAATGGCCTCTAGCCTGG

AGGCTTGCTGAAGGCTGTATGCTGTCATGTTTAAAAATTCGCTGCGCGTT

TTGGCCTCTGACTGACGCGCAGCGAATTTAAACATGACAGGACACAAGGC

CTGTTACTAGCACTCACATGGAACAAATGGCCTCTCTAGAAT 3'

-continued (miRNA expression cassette No. 7-
serotonin receptor 5HT2a):

SEQ ID NO. 7

5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGATGAATCGGG

TTGTCTGAATCGCGTTTTGGCCTCTGACTGACGCGATTCAGAACCCGATT

CATCAGGACACAAGGCCTGTTACTAGCACTCACATGGAACAAATGGCCTC

TAGCCTGGAGGCTTGCTGAAGGCTGTATGCTGAACACTTTGCTATATCAT

CCTGCGTTTTGGCCTCTGACTGACGCAGGATGATAGCAAAGTGTTCAGGA

CACAAGGCCTGTTACTAGCACTCACATGGAACAAATGGCCTCTAGCCTGG

AGGCTTGCTGAAGGCTGTATGCTGTTCTGTTCGTTAAGCTAATGCTCGTT

TTGGCCTCTGACTGACGAGCATTAGCAACGAACAGAACAGGACACAAGGC

CTGTTACTAGCACTCACATGGAACAAATGGCCTCTCTAGAAT 3'

(miRNA expression cassette No. 8-
serotonin receptor 5HT2b):

SEQ ID NO. 8

5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGGAGCATTAGC

AATGCGAACAGAAGTTTTGGCCTCTGACTGACTTCTGTTCGTTGCTAATG

CTCCAGGACACAAGGCCTGTTACTAGCACTCACATGGAACAAATGGCCTC

TAGCCTGGAGGCTTGCTGAAGGCTGTATGCTGAAACATAATGGATTCAGC

AGCGCGTTTTGGCCTCTGACTGACGCGCTGCTGACCATTATGTTTCAGGA

CACAAGGCCTGTTACTAGCACTCACATGGAACAAATGGCCTCTAGCCTGG

AGGCTTGCTGAAGGCTGTATGCTGTTATCTTTGCGAAGCTGCCATCCGTT

TTGGCCTCTGACTGACGGATGGCAGCCGCAAAGATAACAGGACACAAGGC

CTGTTACTAGCACTCACATGGAACAAATGGCCTCTCTAGAAT 3'

(miRNA expression cassette No. 9-
serotonin receptor 5HT2c):

SEQ ID NO. 9

5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGGCTCCTCCAC

TTGGTGGTTTGGTTTTGGCCTCTGACTGACGCGGCAACATTCTGGTGATT

ACAGGACACAAGGCCTGTTACTAGCACTCACATGGAACAAATGGCCTCTA

GCCTGGAGGCTTGCTGAAGGCTGTATGCTGTCATAATCGCTATTTGGTGC

GGCGTTTTGGCCTCTGACTGACGCCGCACCAAAGCGATTATGACAGGACA

CAAGGCCTGTTACTAGCACTCACATGGAACAAATGGCCTCTAGCCTGGAG

GCTTGCTGAAGGCTGTATGCTGTTCTGATCCTGAAGTTCGGGTTCGTTTT

GGCCTCTGACTGACGAACCCGAACCAGGATCAGAACAGGACACAAGGCCT

GTTACTAGCACTCACATGGAACAAATGGCCTCTCTAGAAT 3'

-continued (miRNA expression cassette No. 10-
serotonin receptor 5HT3):

SEQ ID NO. 10

5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGAAATCTTCCG

GTGGTTCCACTGCGTTTTGGCCTCTGACTGACGCAGTGGAACCCGGAAGA

TTTCAGGACACAAGGCCTGTTACTAGCACTCACATGGAACAAATGGCCTC

TAGCCTGGAGGCTTGCTGAAGGCTGTATGCTGATATCCTGAATATGGTAT

GCAGCGTTTTGGCCTCTGACTGACGCTGCATACCATTCAGGATATCAGGA

CACAAGGCCTGTTACTAGCACTCACATGGAACAAATGGCCTCTAGCCTGG

AGGCTTGCTGAAGGCTGTATGCTGTTTAAAGCTCAAACGCGTTCGCCGTT

TTGGCCTCTGACTGACGGCGAACGCGTGAGCTTTAAACAGGACACAAGGC

CTGTTACTAGCACTCACATGGAACAAATGGCCTCTCTAGAAT 3'

(miRNA expression cassette No. 11-
serotonin receptor 5HT4):

SEQ ID NO. 11

5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGTAATAAAGGT

CTGGGAATCACCCGTTTTGGCCTCTGACTGACGGGTGATTCCGACCTTTA

TTACAGGACACAAGGCCTGTTACTAGCACTCACATGGAACAAATGGCCTC

TAGCCTGGAGGCTTGCTGAAGGCTGTATGCTGTAATACGCCAGATCACCA

TCAGCGTTTTGGCCTCTGACTGACGCTGATGGTGCTGGCGTATTACAGGA

CACAAGGCCTGTTACTAGCACTCACATGGAACAAATGGCCTCTAGCCTGG

AGGCTTGCTGAAGGCTGTATGCTGATACAGAAACGAAGGTTCAGGCCGTT

TTGGCCTCTGACTGACGGCCTGAACCCGTTTCTGTATCAGGACACAAGGC

CTGTTACTAGCACTCACATGGAACAAATGGCCTCTCTAGAAT 3'

(miRNA expression cassette No. 12-
serotonin receptor 5HT6):

SEQ ID NO. 12

5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGTCAGATCGCT

GTGGTAAACAGGCGTTTTGGCCTCTGACTGACGCCTGTTTACCAGCGATC

TGACAGGACACAAGGCCTGTTACTAGCACTCACATGGAACAAATGGCCTC

TAGCCTGGAGGCTTGCTGAAGGCTGTATGCTGAGAATCAGATCAGATAGC

GATCCGTTTTGGCCTCTGACTGACGGATCGCTATCTGCTGATTCTCAGGA

CACAAGGCCTGTTACTAGCACTCACATGGAACAAATGGCCTCTAGCCTGG

AGGCTTGCTGAAGGCTGTATGCTGAAACATGCCAACAGCAGAATGCCGTT

TTGGCCTCTGACTGACGGCATTCTGCTGGGCATGTTTCAGGACACAAGGC

CTGTTACTAGCACTCACATGGAACAAATGGCCTCTCTAGAAT 3'

-continued (miRNA expression cassette No. 13-
serotonin receptor 5HT7):

SEQ ID NO. 13
5' GCCACCATGGCCACCGGCTCTCGCACAAGCCTGCTGCTGGCTTTCGGA

CTGCTGTGCCTGCCTTGGCTCCAGGAGGGCTCCGCCGCTAGCATCGATAC

CGTCGCTATGTGCTGGAGGCTTGCTGAAGGCTGTATGCTGACAATCAGAT

ATGGTTGCTCGGCGTTTTGGCCTCTGACTGACGCCGAGCAACTATCTGAT

TGTCAGGACACAAGGCCTGTTACTAGCACTCACATGGAACAAATGGCCTC

TAGCCTGGAGGCTTGCTGAAGGCTGTATGCTGTTTCACAATGCATCGTTC

AGCGCGTTTTGGCCTCTGACTGACGCGCTGAACGGCATTGTGAAACAGGA

CACAAGGCCTGTTACTAGCACTCACATGGAACAAATGGCCTCTAGCCTGG

AGGCTTGCTGAAGGCTGTATGCTGACAATAATGCCAACAGGGTGGTCGTT

TTGGCCTCTGACTGACGACCACCCTGGGCATTATTGTCAGGACACAAGGC

CTGTTACTAGCACTCACATGGAACAAATGGCCTCTCTAGAAT 3'

SEQ ID NO. 14 = SEQ ID NO. 1 + SEQ ID NO. 2
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

-continued
GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

-continued

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGCGGGGGGGG

GCGAGGGGCGGGGGGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCT

TCGCCCCGTGCCCCGCTCCGCCGCCGCCTCGCGCCGCCCGCCCCGGCTCT

-continued

GACTGACCGCGTTACTAAAACAGGTAAGTCCGGCCTCCGCGCCGGGTTTT

GGCGCCTCCCGCGGGCGCCCCCCTCCTCACGGCGAGCGCTGCCACGTCAG

ACGAAGGGCGCAGCGAGCGTCCTGATCCTTCCGCCCGGACGCTCAGGACA

GCGGCCCGCTGCTCATAAGACTCGGCCTTAGAACCCCAGTATCAGCAGAA

GGACATTTTAGGACGGGACTTGGGTGACTCTAGGGCACTGGTTTTCTTTC

CAGAGAGCGGAACAGGCGAGGAAAAGTAGTCCCTTCTCGGCGATTCTGCG

GAGGGATCTCCGTGGGGCGGTGAACGCCGATGATGCCTCTACTAACCATG

TTCATGTTTTCTTTTTTTTTCTACAGGTCCTGGGTGACGAACAGGGTACC

GCCACCATGGCCACCGGCTCTCGCACAAGCCTGCTGCTGGCTTTCGGACT

GCTGTGCCTGCCTTGGCTCCAGGAGGGCTCCGCCGCTAGCATCGATACCG

TCGCTATGTGCTGGAGGCTTGCTGAAGGCTGTATGCTGATCAATCGGATT

GCGGTAATCGCGTTTTGGCCTCTGACTGACGCGATTACCGATCCGATTGA

TCAGGACACAAGGCCTGTTACTAGCACTCACATGGAACAAATGGCCTCTA

GCCTGGAGGCTTGCTGAAGGCTGTATGCTGATCTTTGCTAAATTGGTGCA

CGCGTTTTGGCCTCTGACTGACGCGTGCACCATTAGCAAAGATCAGGACA

CAAGGCCTGTTACTAGCACTCACATGGAACAAATGGCCTCTAGCCTGGAG

GCTTGCTGAAGGCTGTATGCTGACTTCAATCACAATTCCAGCGCCGTTTT

GGCCTCTGACTGACGGCGCTGGAAGTGATTGAAGTCAGGACACAAGGCCT

GTTACTAGCACTCACATGGAACAAATGGCCTCTCTAGAAT 3'

SEQ ID NO. 15 = SEQ ID NO. 1 + SEQ ID NO. 3
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

-continued

```
TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG
```

-continued

```
GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC
```

CTCCCCACCCCCAATTTTGTATTTATTTATTTTTTAATTATTTTGTGCAG

CGATGGGGGCGGGGGGGGGGGGGGGGCGCGCGCCAGGCGGGGCGGGGGGGG

GCGAGGGGCGGGGGGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCT

TCGCCCCGTGCCCCGCTCCGCCGCCGCCTCGCGCCGCCCGCCCCGGCTCT

GACTGACCGCGTTACTAAAACAGGTAAGTCCGGCCTCCGCGCCGGGTTTT

GGCGCCTCCCGCGGGCGCCCCCCTCCTCACGGCGAGCGCTGCCACGTCAG

ACGAAGGGCGCAGCGAGCGTCCTGATCCTTCCGCCCGGACGCTCAGGACA

GCGGCCCGCTGCTCATAAGACTCGGCCTTAGAACCCCAGTATCAGCAGAA

GGACATTTTAGGACGGGACTTGGGTGACTCTAGGGCACTGGTTTTCTTTC

CAGAGAGCGGAACAGGCGAGGAAAAGTAGTCCCTTCTCGGCGATTCTGCG

GAGGGATCTCCGTGGGGCGGTGAACGCCGATGATGCCTCTACTAACCATG

TTCATGTTTTCTTTTTTTTCTACAGGTCCTGGGTGACGAACAGGGTACC

GCCACCATGGCCACCGGCTCTCGCACAAGCCTGCTGCTGGCTTTCGGACT

GCTGTGCCTGCCTTGGCTCCAGGAGGGCTCCGCCGCTAGCATCGATACCG

TCGCTATGTGCTGGAGGCTTGCTGAAGGCTGTATGCTGTAATCTTTCGCT

GGCTGCAGTTCGTTTTGGCCTCTGACTGACGAACTGCAGCGCGAAAGATT

ACAGGACACAAGGCCTGTTACTAGCACTCACATGGAACAAATGGCCTCTA

GCCTGGAGGCTTGCTGAAGGCTGTATGCTGTGTTAATGCTGATGTCACGC

TGCGTTTTGGCCTCTGACTGACGCAGCGTGACCAGCATTAACACAGGACA

CAAGGCCTGTTACTAGCACTCACATGGAACAAATGGCCTCTAGCCTGGAG

GCTTGCTGAAGGCTGTATGCTGTTCACCTGGTTAACACATACACCGTTTT

GGCCTCTGACTGACGGTGTATGTGAACCAGGTGAACAGGACACAAGGCCT

GTTACTAGCACTCACATGGAACAAATGGCCTCTCTAGAAT 3'

SEQ ID NO. 16 = SEQ ID NO. 1 + SEQ ID NO. 4

5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

-continued

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

-continued

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGGATCTCCGTGGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGATTTCTTCCTG

TGCGCTTTCGCCGTTTTGGCCTCTGACTGACGGCGAAAGCGCAGGAAGAA

ATCAGGACACAAGGCCTGTTACTAGCACTCACATGGAACAAATGGCCTCT

AGCCTGGAGGCTTGCTGAAGGCTGTATGCTGAGAATAATCAGATCAGCAC

GCTCGTTTTGGCCTCTGACTGACGAGCGTGCTGCTGATTATTCTCAGGAC

ACAAGGCCTGTTACTAGCACTCACATGGAACAAATGGCCTCTAGCCTGGA

GGCTTGCTGAAGGCTGTATGCTGTAATCAGGCTGAATTCAGATAGCGTTT

TGGCCTCTGACTGACGCTATCTGAACAGCCTGATTACAGGACACAAGGCC

TGTTACTAGCACTCACATGGAACAAATGGCCTCTCTAGAAT 3'

SEQ ID NO. 17 = SEQ ID NO. 1 + SEQ ID NO. 5
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

-continued

```
GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC
```

-continued

```
GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG
```

-continued

```
CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGATAATCACCGC

TGCAGGTTCAGCGTTTTGGCCTCTGACTGACGCTGAACCTGGCGGTGATT

ATCAGGACACAAGGCCTGTTACTAGCACTCACATGGAACAAATGGCCTCT

AGCCTGGAGGCTTGCTGAAGGCTGTATGCTGTTCAATCGCGTATTGGTAA

TCGCGTTTTGGCCTCTGACTGACGCGATTACCAACGCGATTGAACAGGAC

ACAAGGCCTGTTACTAGCACTCACATGGAACAAATGGCCTCTAGCCTGGA

GGCTTGCTGAAGGCTGTATGCTGTGATCATGCTGAAAATGGTGCACGTTT

TGGCCTCTGACTGACGTGCACCATTCAGCATGATCACAGGACACAAGGCC

TGTTACTAGCACTCACATGGAACAAATGGCCTCTCTAGAAT 3'
```

SEQ ID NO. 18 = SEQ ID NO. 1 + SEQ ID NO. 6

```
5' AATCAACCTCTGGATTACAAAATTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA
```

-continued

```
AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC
```

-continued

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

-continued

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGGGGGCGGGG

CGAGGGGCGGGGCGGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGGGGGGAGTCGCTGCGCGCTGCCTTC

GCCCCGTGCCCCGCTCCGCCGCCGCCTCGCGCCGCCCGCCCCGGCTCTGA

CTGACCGCGTTACTAAAACAGGTAAGTCCGGCCTCCGCGCCGGGTTTTGG

CGCCTCCCGCGGGCGCCCCCCTCCTCACGGCGAGCGCTGCCACGTCAGAC

GAAGGGCGCAGCGAGCGTCCTGATCCTTCCGCCCGGACGCTCAGGACAGC

GGCCCGCTGCTCATAAGACTCGGCCTTAGAACCCCAGTATCAGCAGAAGG

ACATTTTAGGACGGGACTTGGGTGACTCTAGGGCACTGGTTTTCTTTCCA

GAGAGCGGAACAGGCGAGGAAAAGTAGTCCCTTCTCGGCGATTCTGCGGA

GGGATCTCCGTGGGGCGGTGAACGCCGATGATGCCTCTACTAACCATGTT

CATGTTTTCTTTTTTTTTCTACAGGTCCTGGGTGACGAACAGGGTACCGC

CACCATGGCCACCGGCTCTCGCACAAGCCTGCTGCTGGCTTTCGGACTGC

TGTGCCTGCCTTGGCTCCAGGAGGGCTCCGCCGCTAGCATCGATACCGTC

GCTATGTGCTGGAGGCTTGCTGAAGGCTGTATGCTGAGGTAATATCCTGA

CGCTCAGCCGTTTTGGCCTCTGACTGACGGCTGAGCGTGGATATTACCTC

AGGACACAAGGCCTGTTACTAGCACTCACATGGAACAAATGGCCTCTAGC

CTGGAGGCTTGCTGAAGGCTGTATGCTGTACAGAATCAGATAATCAGCGC

CGTTTTGGCCTCTGACTGACGGCGCTGATTCTGATTCTGTACAGGACACA

AGGCCTGTTACTAGCACTCACATGGAACAAATGGCCTCTAGCCTGGAGGC

TTGCTGAAGGCTGTATGCTGTCATGTTTAAAAAATTCGCTGCGCGTTTTGG

-continued

CCTCTGACTGACGCGCAGCGAATTTAAACATGACAGGACACAAGGCCTGT

TACTAGCACTCACATGGAACAAATGGCCTCTCTAGAAT 3'

SEQ ID NO. 19 = SEQ ID NO. 1 + SEQ ID NO. 7
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

-continued

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTTCCGAAGGTAACTGGCTTCAGCAGAGCGCAGATACCAA

ATACTGTCCTTCTAGTGTAGCCGTAGTTAGGCCACCACTTCAAGAACTCT

-continued

```
GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGATGAATCGGGT
```

-continued

```
TGTCTGAATCGCGTTTTGGCCTCTGACTGACGCGATTCAGAACCCGATTC

ATCAGGACACAAGGCCTGTTACTAGCACTCACATGGAACAAATGGCCTCT

AGCCTGGAGGCTTGCTGAAGGCTGTATGCTGAACACTTTGCTATATCATC

CTGCGTTTTGGCCTCTGACTGACGCAGGATGATAGCAAAGTGTTCAGGAC

ACAAGGCCTGTTACTAGCACTCACATGGAACAAATGGCCTCTAGCCTGGA

GGCTTGCTGAAGGCTGTATGCTGTTCTGTTCGTTAAGCTAATGCTCGTTT

TGGCCTCTGACTGACGAGCATTAGCAACGAACAGAACAGGACACAAGGCC

TGTTACTAGCACTCACATGGAACAAATGGCCTCTCTAGAAT 3'

SEQ ID NO. 20 = SEQ ID NO. 1 + SEQ ID NO. 8
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA
```

-continued

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

-continued

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCAATTTTGTATTTATTTATTTTTTAATTATTTTGTGCAG

CGATGGGGGCGGGGGGGGGGGGGGGCGCGCGCCAGGCGGGGCGGGGGGG

GCGAGGGGCGGGGGGGGCGAGGCGGAGAGGTGCGGCGGCAGCCAATCAGA

GCGGCGCGCTCCGAAAGTTTCCTTTTATGGCGAGGCGGCGGCGGCGGCGG

CCCTATAAAAAGCGAAGCGCGCGGCGGGCGGGAGTCGCTGCGCGCTGCCT

TCGCCCCGTGCCCCGCTCCGCCGCCGCCTCGCGCCGCCCGCCCCGGCTCT

GACTGACCGCGTTACTAAAACAGGTAAGTCCGGCCTCCGCGCCGGGTTTT

GGCGCCTCCCGCGGGCGCCCCCCTCCTCACGGCGAGCGCTGCCACGTCAG

ACGAAGGGCGCAGCGAGCGTCCTGATCCTTCCGCCCGGACGCTCAGGACA

GCGGCCCGCTGCTCATAAGACTCGGCCTTAGAACCCCAGTATCAGCAGAA

GGACATTTTAGGACGGGACTTGGGTGACTCTAGGGCACTGGTTTTCTTTC

CAGAGAGCGGAACAGGCGAGGAAAAGTAGTCCCTTCTCGGCGATTCTGCG

GAGGGATCTCCGTGGGGCGGTGAACGCCGATGATGCCTCTACTAACCATG

TTCATGTTTTCTTTTTTTTTCTACAGGTCCTGGGTGACGAACAGGGTACC

GCCACCATGGCCACCGGCTCTCGCACAAGCCTGCTGCTGGCTTTCGGACT

GCTGTGCCTGCCTTGGCTCCAGGAGGGCTCCGCCGCTAGCATCGATACCG

TCGCTATGTGCTGGAGGCTTGCTGAAGGCTGTATGCTGGAGCATTAGCAA

TGCGAACAGAAGTTTTGGCCTCTGACTGACTTCTGTTCGTTGCTAATGCT

CCAGGACACAAGGCCTGTTACTAGCACTCACATGGAACAAATGGCCTCTA

GCCTGGAGGCTTGCTGAAGGCTGTATGCTGAAACATAATGGATTCAGCAG

CGCGTTTTGGCCTCTGACTGACGCGCTGCTGACCATTATGTTTCAGGACA

CAAGGCCTGTTACTAGCACTCACATGGAACAAATGGCCTCTAGCCTGGAG

GCTTGCTGAAGGCTGTATGCTGTTATCTTTGCGAAGCTGCCATCCGTTTT

GGCCTCTGACTGACGGATGGCAGCCGCAAAGATAACAGGACACAAGGCCT

GTTACTAGCACTCACATGGAACAAATGGCCTCTCTAGAAT 3'

SEQ ID NO. 21 = SEQ ID NO. 1 + SEQ ID NO. 9
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

-continued

```
TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTTATGGCGAGGCGGCGGCGGCGGCG

GCCCTATAAAAAGCGAAGCGCGCGGCGGGCGGGAGTCGCTGCGCGCTGCC
```

-continued

```
TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGGCTCCTCCACT

TGGTGGTTTGGTTTTGGCCTCTGACTGACGCGGCAACATTCTGGTGATTA

CAGGACACAAGGCCTGTTACTAGCACTCACATGGAACAAATGGCCTCTAG

CCTGGAGGCTTGCTGAAGGCTGTATGCTGTCATAATCGCTATTTGGTGCG

GCGTTTTGGCCTCTGACTGACGCCGCACCAAAGCGATTATGACAGGACAC

AAGGCCTGTTACTAGCACTCACATGGAACAAATGGCCTCTAGCCTGGAGG

CTTGCTGAAGGCTGTATGCTGTTCTGATCCTGAAGTTCGGGTTCGTTTTG

GCCTCTGACTGACGAACCCGAACCAGGATCAGAACAGGACACAAGGCCTG

TTACTAGCACTCACATGGAACAAATGGCCTCTCTAGAAT 3'
```

SEQ ID NO. 22 = SEQ ID NO. 1 + SEQ ID NO. 10

```
5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC
```

-continued

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

-continued

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

-continued

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGCGGGGGGGG

GCGAGGGGCGGGGCGGGGCGAGGCGGAGAGGTGCGGCGGCAGCCAATCAG

AGCGGCGCGCTCCGAAAGTTTCCTTTTATGGCGAGGCGGCGGCGGCGGCG

GCCCTATAAAAAGCGAAGCGCGCGGCGGGCGGGAGTCGCTGCGCGCTGCC

TTCGCCCCGTGCCCCGCTCCGCCGCCGCCTCGCGCCGCCCGCCCCGGCTC

TGACTGACCGCGTTACTAAAACAGGTAAGTCCGGCCTCCGCGCCGGGTTT

TGGCGCCTCCCGCGGGCGCCCCCCTCCTCACGGCGAGCGCTGCCACGTCA

GACGAAGGGCGCAGCGAGCGTCCTGATCCTTCCGCCCGGACGCTCAGGAC

AGCGGCCCGCTGCTCATAAGACTCGGCCTTAGAACCCCAGTATCAGCAGA

AGGACATTTTAGGACGGGACTTGGGTGACTCTAGGGCACTGGTTTTCTTT

CCAGAGAGCGGAACAGGCGAGGAAAAGTAGTCCCTTCTCGGCGATTCTGC

GGAGGGATCTCCGTGGGGCGGTGAACGCCGATGATGCCTCTACTAACCAT

GTTCATGTTTTCTTTTTTTTTCTACAGGTCCTGGGTGACGAACAGGGTAC

CGCCACCATGGCCACCGGCTCTCGCACAAGCCTGCTGCTGGCTTTCGGAC

TGCTGTGCCTGCCTTGGCTCCAGGAGGGCTCCGCCGCTAGCATCGATACC

GTCGCTATGTGCTGGAGGCTTGCTGAAGGCTGTATGCTGAAATCTTCCGG

TGGTTCCACTGCGTTTTGGCCTCTGACTGACGCAGTGGAACCCGGAAGAT

TTCAGGACACAAGGCCTGTTACTAGCACTCACATGGAACAAATGGCCTCT

AGCCTGGAGGCTTGCTGAAGGCTGTATGCTGATATCCTGAATATGGTATG

CAGCGTTTTGGCCTCTGACTGACGCTGCATACCATTCAGGATATCAGGAC

ACAAGGCCTGTTACTAGCACTCACATGGAACAAATGGCCTCTAGCCTGGA

GGCTTGCTGAAGGCTGTATGCTGTTTAAAGCTCAAACGCGTTCGCCGTTT

TGGCCTCTGACTGACGGCGAACGCGTGAGCTTTAAACAGGACACAAGGCC

TGTTACTAGCACTCACATGGAACAAATGGCCTCTCTAGAAT 3'

SEQ ID NO. 23 = SEQ ID NO:. 1 + SEQ ID NO. 11

5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

-continued

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

-continued

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

-continued

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGGGGGCGGGG

CGAGGGGGGGGCGGGGCGAGGCGGAGAGGTGCGGCGGCAGCCAATCAGAG

CGGCGCGCTCCGAAAGTTTCCTTTTATGGCGAGGCGGCGGCGGCGGCGGC

CCTATAAAAAGCGAAGCGCGCGGCGGGCGGGAGTCGCTGCGCGCTGCCTT

CGCCCCGTGCCCCGCTCCGCCGCCGCCTCGCGCCGCCCGCCCCGGCTCTG

ACTGACCGCGTTACTAAAACAGGTAAGTCCGGCCTCCGCGCCGGGTTTTG

GCGCCTCCCGCGGGCGCCCCCCTCCTCACGGCGAGCGCTGCCACGTCAGA

CGAAGGGCGCAGCGAGCGTCCTGATCCTTCCGCCCGGACGCTCAGGACAG

CGGCCCGCTGCTCATAAGACTCGGCCTTAGAACCCCAGTATCAGCAGAAG

GACATTTTAGGACGGGACTTGGGTGACTCTAGGGCACTGGTTTTCTTTCC

AGAGAGCGGAACAGGCGAGGAAAAGTAGTCCCTTCTCGGCGATTCTGCGG

AGGGATCTCCGTGGGGCGGTGAACGCCGATGATGCCTCTACTAACCATGT

TCATGTTTTCTTTTTTTTTCTACAGGTCCTGGGTGACGAACAGGGTACCG

CCACCATGGCCACCGGCTCTCGCACAAGCCTGCTGCTGGCTTTCGGACTG

CTGTGCCTGCCTTGGCTCCAGGAGGGCTCCGCCGCTAGCATCGATACCGT

CGCTATGTGCTGGAGGCTTGCTGAAGGCTGTATGCTGTAATAAAGGTCTG

GGAATCACCCGTTTTGGCCTCTGACTGACGGGTGATTCCGACCTTTATTA

CAGGACACAAGGCCTGTTACTAGCACTCACATGGAACAAATGGCCTCTAG

CCTGGAGGCTTGCTGAAGGCTGTATGCTGTAATACGCCAGATCACCATCA

GCGTTTTGGCCTCTGACTGACGCTGATGGTGCTGGCGTATTACAGGACAC

AAGGCCTGTTACTAGCACTCACATGGAACAAATGGCCTCTAGCCTGGAGG

CTTGCTGAAGGCTGTATGCTGATACAGAAACGAAGGTTCAGGCCGTTTTG

GCCTCTGACTGACGGCCTGAACCCGTTTCTGTATCAGGACACAAGGCCTG

TTACTAGCACTCACATGGAACAAATGGCCTCTCTAGAAT 3'

SEQ ID NO. 24 = SEQ ID NO. 1 + SEQ ID NO. 12

5' AATCAACCTCTGGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

-continued

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG

TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

-continued

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC

CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

-continued

```
GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGCGCGCGCCAGGCGGGGGGGGGGGGG

CGAGGGGCGGGGGGGCGAGGCGGAGAGGTGCGGCGGCAGCCAATCAGAG

CGGCGCGCTCCGAAAGTTTCCTTTTATGGCGAGGCGGCGGCGGCGGCGGC

CCTATAAAAAGCGAAGCGCGCGGCGGGCGGGAGTCGCTGCGCGCTGCCTT

CGCCCCGTGCCCCGCTCCGCCGCCGCCTCGCGCCGCCCGCCCCGGCTCTG

ACTGACCGCGTTACTAAAACAGGTAAGTCCGGCCTCCGCGCCGGGTTTTG

GCGCCTCCCGCGGGCGCCCCCCTCCTCACGGCGAGCGCTGCCACGTCAGA

CGAAGGGCGCAGCGAGCGTCCTGATCCTTCCGCCCGGACGCTCAGGACAG

CGGCCCGCTGCTCATAAGACTCGGCCTTAGAACCCCAGTATCAGCAGAAG

GACATTTTAGGACGGGACTTGGGTGACTCTAGGGCACTGGTTTTCTTTCC

AGAGAGCGGAACAGGCGAGGAAAAGTAGTCCCTTCTCGGCGATTCTGCGG

AGGGATCTCCGTGGGGCGGTGAACGCCGATGATGCCTCTACTAACCATGT

TCATGTTTTCTTTTTTTTTCTACAGGTCCTGGGTGACGAACAGGGTACCG

CCACCATGGCCACCGGCTCTCGCACAAGCCTGCTGCTGGCTTTCGGACTG

CTGTGCCTGCCTTGGCTCCAGGAGGGCTCCGCCGCTAGCATCGATACCGT

CGCTATGTGCTGGAGGCTTGCTGAAGGCTGTATGCTGTCAGATCGCTGTG

GTAAACAGGCGTTTTGGCCTCTGACTGACGCCTGTTTACCAGCGATCTGA

CAGGACACAAGGCCTGTTACTAGCACTCACATGGAACAAATGGCCTCTAG

CCTGGAGGCTTGCTGAAGGCTGTATGCTGAGAATCAGATCAGATAGCGAT

CCGTTTTGGCCTCTGACTGACGGATCGCTATCTGCTGATTCTCAGGACAC

AAGGCCTGTTACTAGCACTCACATGGAACAAATGGCCTCTAGCCTGGAGG

CTTGCTGAAGGCTGTATGCTGAAACATGCCAACAGCAGAATGCCGTTTTG

GCCTCTGACTGACGGCATTCTGCTGGGCATGTTTCAGGACACAAGGCCTG

TTACTAGCACTCACATGGAACAAATGGCCTCTCTAGAAT 3'
```

SEQ ID NO. 25 = SEQ ID NO. 1 + SEQ ID NO. 13
5' AATCAACCTCTGGATTACAAAATTTGTGAAAGATTGACTGGTATTCTT

AACTATGTTGCTCCTTTTACGCTATGTGGATACGCTGCTTTAATGCCTTT

-continued

```
GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCTAAGCTTA

TCGATACCGTCGAGATCTAACTTGTTTATTGCAGCTTATAATGGTTACAA

ATAAAGCAATAGCATCACAAATTTCACAAATAAAGCATTTTTTTCACTGC

ATTCTAGTTGTGGTTTGTCCAAACTCATCAATGTATCTTATCATGTCTGG

ATCTCGACCTCGACTAGAGCATGGCTACGTAGATAAGTAGCATGGCGGGT

TAATCATTAACTACAAGGAACCCCTAGTGATGGAGTTGGCCACTCCCTCT

CTGCGCGCTCGCTCGCTCACTGAGGCCGGGCGACCAAAGGTCGCCCGACG

CCCGGGCTTTGCCCGGGCGGCCTCAGTGAGCGAGCGAGCGCGCAGCTGGC

GTAATAGCGAAGAGGCCCGCACCGATCGCCCTTCCCAACAGTTGCGCAGC

CTGAATGGCGAATGGCGATTCCGTTGCAATGGCTGGCGGTAATATTGTTC

TGGATATTACCAGCAAGGCCGATAGTTTGAGTTCTTCTACTCAGGCAAGT

GATGTTATTACTAATCAAAGAAGTATTGCGACAACGGTTAATTTGCGTGA

TGGACAGACTCTTTTACTCGGTGGCCTCACTGATTATAAAAACACTTCTC

AGGATTCTGGCGTACCGTTCCTGTCTAAAATCCCTTTAATCGGCCTCCTG

TTTAGCTCCCGCTCTGATTCTAACGAGGAAAGCACGTTATACGTGCTCGT

CAAAGCAACCATAGTACGCGCCCTGTAGCGGCGCATTAAGCGCGGCGGGT

GTGGTGGTTACGCGCAGCGTGACCGCTACACTTGCCAGCGCCCTAGCGCC

CGCTCCTTTCGCTTTCTTCCCTTCCTTTCTCGCCACGTTCGCCGGCTTTC

CCCGTCAAGCTCTAAATCGGGGGCTCCCTTTAGGGTTCCGATTTAGTGCT

TTACGGCACCTCGACCCCAAAAAACTTGATTAGGGTGATGGTTCACGTAG

TGGGCCATCGCCCTGATAGACGGTTTTTCGCCCTTTGACGTTGGAGTCCA

CGTTCTTTAATAGTGGACTCTTGTTCCAAACTGGAACAACACTCAACCCT

ATCTCGGTCTATTCTTTTGATTTATAAGGGATTTTGCCGATTTCGGCCTA

TTGGTTAAAAAATGAGCTGATTTAACAAAAATTTAACGCGAATTTTAACA

AAATATTAACGTTTACAATTTAAATATTTGCTTATACAATCTTCCTGTTT

TTGGGGCTTTTCTGATTATCAACCGGGGTACATATGATTGACATGCTAGT

TTTACGATTACCGTTCATCGATTCTCTTGTTTGCTCCAGACTCTCAGGCA

ATGACCTGATAGCCTTTGTAGAGACCTCTCAAAAATAGCTACCCTCTCCG

GCATGAATTTATCAGCTAGAACGGTTGAATATCATATTGATGGTGATTTG

ACTGTCTCCGGCCTTTCTCACCCGTTTGAATCTTTACCTACACATTACTC

AGGCATTGCATTTAAAATATATGAGGGTTCTAAAAATTTTTATCCTTGCG
```

-continued

```
TTGAAATAAAGGCTTCTCCCGCAAAAGTATTACAGGGTCATAATGTTTTT

GGTACAACCGATTTAGCTTTATGCTCTGAGGCTTTATTGCTTAATTTTGC

TAATTCTTTGCCTTGCCTGTATGATTTATTGGATGTTGGAATTCCTGATG

CGGTATTTTCTCCTTACGCATCTGTGCGGTATTTCACACCGCATATGGTG

CACTCTCAGTACAATCTGCTCTGATGCCGCATAGTTAAGCCAGCCCCGAC

ACCCGCCAACACCCGCTGACGCGCCCTGACGGGCTTGTCTGCTCCCGGCA

TCCGCTTACAGACAAGCTGTGACCGTCTCCGGGAGCTGCATGTGTCAGAG

GTTTTCACCGTCATCACCGAAACGCGCGAGACGAAAGGGCCTCGTGATAC

GCCTATTTTTATAGGTTAATGTCATGATAATAATGGTTTCTTAGACGTCA

GGTGGCACTTTTCGGGGAAATGTGCGCGGAACCCCTATTTGTTTATTTTT

CTAAATACATTCAAATATGTATCCGCTCATGAGACAATAACCCTGATAAA

TGCTTCAATAATATTGAAAAAGGAAGAGTATGAGTATTCAACATTTCCGT

GTCGCCCTTATTCCCTTTTTTGCGGCATTTTGCCTTCCTGTTTTTGCTCA

CCCAGAAACGCTGGTGAAAGTAAAAGATGCTGAAGATCAGTTGGGTGCAC

GAGTGGGTTACATCGAACTGGATCTCAACAGCGGTAAGATCCTTGAGAGT

TTTCGCCCCGAAGAACGTTTTCCAATGATGAGCACTTTTAAAGTTCTGCT

ATGTGGCGCGGTATTATCCCGTATTGACGCCGGGCAAGAGCAACTCGGTC

GCCGCATACACTATTCTCAGAATGACTTGGTTGAGTACTCACCAGTCACA

GAAAAGCATCTTACGGATGGCATGACAGTAAGAGAATTATGCAGTGCTGC

CATAACCATGAGTGATAACACTGCGGCCAACTTACTTCTGACAACGATCG

GAGGACCGAAGGAGCTAACCGCTTTTTTGCACAACATGGGGGATCATGTA

ACTCGCCTTGATCGTTGGGAACCGGAGCTGAATGAAGCCATACCAAACGA

CGAGCGTGACACCACGATGCCTGTAGCAATGGCAACAACGTTGCGCAAAC

TATTAACTGGCGAACTACTTACTCTAGCTTCCCGGCAACAATTAATAGAC

TGGATGGAGGCGGATAAAGTTGCAGGACCACTTCTGCGCTCGGCCCTTCC

GGCTGGCTGGTTTATTGCTGATAAATCTGGAGCCGGTGAGCGTGGGTCTC

GCGGTATCATTGCAGCACTGGGGCCAGATGGTAAGCCCTCCCGTATCGTA

GTTATCTACACGACGGGGAGTCAGGCAACTATGGATGAACGAAATAGACA

GATCGCTGAGATAGGTGCCTCACTGATTAAGCATTGGTAACTGTCAGACC

AAGTTTACTCATATATACTTTAGATTGATTTAAAACTTCATTTTTAATTT

AAAAGGATCTAGGTGAAGATCCTTTTTTGATAATCTCATGACCAAAATCCC

TTAACGTGAGTTTTCGTTCCACTGAGCGTCAGACCCCGTAGAAAAGATCA

AAGGATCTTCTTGAGATCCTTTTTTTCTGCGCGTAATCTGCTGCTTGCAA

ACAAAAAAACCACCGCTACCAGCGGTGGTTTGTTTGCCGGATCAAGAGCT

ACCAACTCTTTTTCCGAAGGTAACTGGCTTCAGCAGAGCGCAGATACCAA

ATACTGTCCTTCTAGTGTAGCCGTAGTTAGGCCACCACTTCAAGAACTCT

GTAGCACCGCCTACATACCTCGCTCTGCTAATCCTGTTACCAGTGGCTGC

TGCCAGTGGCGATAAGTCGTGTCTTACCGGGTTGGACTCAAGACGATAGT

TACCGGATAAGGCGCAGCGGTCGGGCTGAACGGGGGGTTCGTGCACACAG

CCCAGCTTGGAGCGAACGACCTACACCGAACTGAGATACCTACAGCGTGA

GCTATGAGAAAGCGCCACGCTTCCCGAAGGGAGAAAGGCGGACAGGTATC
```

-continued

```
CGGTAAGCGGCAGGGTCGGAACAGGAGAGCGCACGAGGGAGCTTCCAGGG

GGAAACGCCTGGTATCTTTATAGTCCTGTCGGGTTTCGCCACCTCTGACT

TGAGCGTCGATTTTTGTGATGCTCGTCAGGGGGGCGGAGCCTATGGAAAA

ACGCCAGCAACGCGGCCTTTTTACGGTTCCTGGCCTTTTGCTGGCCTTTT

GCTCACATGTTCTTTCCTGCGTTATCCCCTGATTCTGTGGATAACCGTAT

TACCGCCTTTGAGTGAGCTGATACCGCTCGCCGCAGCCGAACGACCGAGC

GCAGCGAGTCAGTGAGCGAGGAAGCGGAAGAGCGCCCAATACGCAAACCG

CCTCTCCCCGCGCGTTGGCCGATTCATTAATGCAGCAGCTGCGCGCTCGC

TCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACT

CCATCACTAGGGGTTCCTTGTAGTTAATGATTAACCCGCCATGCTACTTA

TCTACGTAGCCATGCTCTAGGACATTGATTATTGACTAGTGGAGTTCCGC

GTTACATAACTTACGGTAAATGGCCCGCCTGGCTGACCGCCCAACGACCC

CCGCCCATTGACGTCAATAATGACGTATGTTCCCATAGTAACGCCAATAG

GGACTTTCCATTGACGTCAATGGGTGGAGTATTTACGGTAAACTGCCCAC

TTGGCAGTACATCAAGTGTATCATATGCCAAGTACGCCCCCTATTGACGT

CAATGACGGTAAATGGCCCGCCTGGCATTATGCCCAGTACATGACCTTAT

GGGACTTTCCTACTTGGCAGTACATCTACGTATTAGTCATCGCTATTACC

ATGGTCGAGGTGAGCCCCACGTTCTGCTTCACTCTCCCCATCTCCCCCCC

CTCCCCACCCCCAATTTTGTATTTATTTATTTTTTAATTATTTTGTGCAG

CGATGGGGGCGGGGGGGGGGGGGGGCGCGCGCCAGGCGGGGGGGGGGGGG

CGAGGGGCGGGGGGGGCGAGGCGGAGAGGTGCGGCGGCAGCCAATCAGAG

CGGCGCGCTCCGAAAGTTTCCTTTTATGGCGAGGCGGCGGCGGCGGCGGC

CCTATAAAAAGCGAAGCGCGCGGCGGGGGGAGTCGCTGCGCGCTGCCTTC

GCCCCGTGCCCCGCTCCGCCGCCGCCTCGCGCCGCCCGCCCCGGCTCTGA

CTGACCGCGTTACTAAAACAGGTAAGTCCGGCCTCCGCGCCGGGTTTTGG

CGCCTCCCGCGGGCGCCCCCCTCCTCACGGCGAGCGCTGCCACGTCAGAC

GAAGGGCGCAGCGAGCGTCCTGATCCTTCCGCCCGGACGCTCAGGACAGC

GGCCCGCTGCTCATAAGACTCGGCCTTAGAACCCCAGTATCAGCAGAAGG

ACATTTTAGGACGGGACTTGGGTGACTCTAGGGCACTGGTTTTCTTTCCA

GAGAGCGGAACAGGCGAGGAAAAGTAGTCCCTTCTCGGCGATTCTGCGGA

GGGATCTCCGTGGGCGGTGAACGCCGATGATGCCTCTACTAACCATGTT

CATGTTTTCTTTTTTTTTCTACAGGTCCTGGGTGACGAACAGGGTACCGC

CACCATGGCCACCGGCTCTCGCACAAGCCTGCTGCTGGCTTTCGGACTGC

TGTGCCTGCCTTGGCTCCAGGAGGGCTCCGCCGCTAGCATCGATACCGTC

GCTATGTGCTGGAGGCTTGCTGAAGGCTGTATGCTGACAATCAGATATGG

TTGCTCGGCGTTTTGGCCTCTGACTGACGCCGAGCAACTATCTGATTGTC

AGGACACAAGGCCTGTTACTAGCACTCACATGGAACAAATGGCCTCTAGC

CTGGAGGCTTGCTGAAGGCTGTATGCTGTTTCACAATGCATCGTTCAGCG

CGTTTTGGCCTCTGACTGACGCGCTGAACGGCATTGTGAAACAGGACACA
```

-continued

```
AGGCCTGTTACTAGCACTCACATGGAACAAATGGCCTCTAGCCTGGAGGC

TTGCTGAAGGCTGTATGCTGACAATAATGCCAACAGGGTGGTCGTTTTGG

CCTCTGACTGACGACCACCCTGGGCATTATTGTCAGGACACAAGGCCTGT      5

TACTAGCACTCACATGGAACAAATGGCCTCTCTAGAAT 3'
```

As will be appreciated by those skilled in the art, because the recombinant plasmid is a circular vector, the one or more sequences of the miRNA expression cassettes may be connected at the 3' end of SEQ ID NO. 1, as shown in SEQ ID NO. 14, SEQ ID NO. 15, SEQ ID NO. 16, SEQ ID NO. 17, SEQ ID NO. 18, SEQ ID NO. 19, SEQ ID NO. 20, SEQ ID NO. 21, SEQ ID NO. 22, SEQ ID NO. 23, SEQ ID NO. 24 and SEQ ID NO. 25, or at the 5' end of SEQ ID NO. 1.

As will be appreciated by those skilled in the art, a perfect match of nucleotides with each of the miRNA expression cassette sequences is not necessary in order to have the desired result of decreased bioavailability of the target biomolecule as a result of the target cell producing the miRNA sequence that will bind to and degrade the mRNA of the target biomolecule. In some embodiments of the present disclosure, about 80% to about 100% nucleotide sequence matching with each of the miRNA expression cassettes causes the desired result. In some embodiments of the present disclosure, about 85% to about 100% nucleotide sequence matching with each of the miRNA expression cassettes causes the desired result. In some embodiments of the present disclosure, about 90% to about 100% nucleotide sequence matching with each of the miRNA expression cassettes causes the desired result. In some embodiments of the present disclosure, about 95% to about 100% nucleotide sequence matching with each of the miRNA expression cassettes causes the desired result.

Example 1—Expression Cassette

Expression cassettes for expressing miRNA were synthesized. The synthesized miRNA expression cassettes were cloned into the pAVA-00200 plasmid backbone containing the CASI promoter, multiple cloning site (MCS), Woodchuck Hepatitis Virus post-transcriptional regulatory element (WPRE), and Simian virus 40 (SV40) polyadenylation (polyA) sequence, all flanked by the AAV2 inverted terminal repeats (ITR). pAVA-00200 was cut with the restriction enzymes KpnI and XbaI in the MCS and separated on a 1% agarose gel. The band of interest was excised and purified using a gel extraction kit. Each miRNA expression cassette was amplified by polymerase chain reaction (PCR) using Taq polymerase and the PCR products were gel purified and the bands on interest were also excised and purified using a gel extraction kit. These PCR products contained the miRNA expression cassettes in addition to 15 base pair 5' and 3' overhangs that aligned with the ends of the linearized pAVA-00200 backbone. Using in-fusion cloning, the amplified miRNA expression cassettes were integrated with the pAVA-00200 backbone via homologous recombination. The resulting RP contained the following: 5' ITR, CASI promoter, miRNA expression cassette, WPRE, SV40 polyA and ITR 3'.

The invention claimed is:

1. A composition that comprises a recombinant plasmid (RP) that comprises a sequence of nucleotides that is SEQ ID NO 14.

2. The composition of claim 1, wherein the RP is encapsulated in: a protein coat, a lipid vesicle, or any combination thereof.

* * * * *